(12) United States Patent
Hitchcock et al.

(10) Patent No.: US 11,709,118 B2
(45) Date of Patent: Jul. 25, 2023

(54) LOST CIRCULATION MATERIALS (LCM) AND LOST CIRCULATION SHAPES (LCS) TEST FIXTURE

(71) Applicant: SAUDI ARABIAN OIL COMPANY, Dhahran (SA)

(72) Inventors: Graham Hitchcock, Aberdeenshire (GB); Michael Anthony Affleck, Aberdeen (GB); Christopher Thomas Wrighton, Aberdeenshire (GB)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 167 days.

(21) Appl. No.: 17/168,650

(22) Filed: Feb. 5, 2021

(65) Prior Publication Data

US 2021/0254450 A1    Aug. 19, 2021

Related U.S. Application Data

(60) Provisional application No. 62/976,033, filed on Feb. 13, 2020.

(51) Int. Cl.
*G01N 11/04* (2006.01)
*E21B 47/09* (2012.01)
(Continued)

(52) U.S. Cl.
CPC ............ *G01N 11/04* (2013.01); *E21B 21/003* (2013.01); *E21B 47/09* (2013.01); *G01N 33/24* (2013.01);
(Continued)

(58) Field of Classification Search
CPC ...... G01N 11/04; G01N 33/24; G01N 33/241; G01N 33/2823; E21B 21/003; E21B 47/09
See application file for complete search history.

(56) References Cited

U.S. PATENT DOCUMENTS

| 2,733,595 A | 2/1956 | Twining |
| 5,803,666 A | 9/1998 | Keller |

(Continued)

FOREIGN PATENT DOCUMENTS

| AU | 2008225088 B2 | 12/2014 |
| AU | 2015264796 A1 | 12/2015 |

(Continued)

OTHER PUBLICATIONS

International Search Report and Written Opinion issued in Application No. PCT/US2021/017420, dated Apr. 26, 2021 (45 pages).

*Primary Examiner* — Ryan D Walsh

(74) *Attorney, Agent, or Firm* — Osha Bergman Watanabe & Burton LLP

(57) ABSTRACT

A testing apparatus for testing a fluid and a loss control material (LCM) is provided. The testing apparatus includes a testing chamber having an upstream end, a downstream end, a device central axis, and a general flow direction. The testing chamber includes a chamber body having an upstream cap, a downstream cap, a first chamber wall, and a second chamber wall. The first chamber wall has a first diameter and in part defines a first chamber interior, the second chamber wall has a second diameter, the first diameter is less than the second diameter, and both the first chamber wall and the second chamber wall are positioned relative to one another such that an annulus is defined in part in between. The traversal of the fluid and the LCM along the fluid flow path is restricted by a flow restriction.

19 Claims, 13 Drawing Sheets

(51) Int. Cl.
*G01N 33/24* (2006.01)
*E21B 21/00* (2006.01)
*G01N 33/28* (2006.01)

(52) U.S. Cl.
CPC ....... *G01N 33/241* (2013.01); *G01N 33/2823* (2013.01)

(56) References Cited

U.S. PATENT DOCUMENTS

| | | |
|---|---|---|
| 6,170,531 B1 | 1/2001 | Jung et al. |
| 8,567,491 B2 | 10/2013 | Lurie |
| 8,573,048 B2 * | 11/2013 | Slater ................ G01N 33/2823 73/152.01 |
| 9,285,355 B2 | 3/2016 | Murphy et al. |
| 11,111,742 B2 * | 9/2021 | Amanullah ............ G01N 11/00 |
| 2009/0029878 A1 | 1/2009 | Bicerano |
| 2010/0193244 A1 | 8/2010 | Hoskins |
| 2013/0192358 A1 | 8/2013 | Murphy et al. |
| 2014/0102188 A1 | 4/2014 | Murphy et al. |
| 2014/0182369 A1 | 7/2014 | Blue et al. |
| 2015/0008044 A1 | 1/2015 | Fontenot |
| 2015/0020908 A1 | 1/2015 | Warren |
| 2018/0266197 A1 * | 9/2018 | Amanullah ............ E21B 49/08 |
| 2020/0248527 A1 | 8/2020 | Hitchcock |
| 2020/0370431 A1 * | 11/2020 | Amanullah ........... E21B 49/087 |

FOREIGN PATENT DOCUMENTS

| | | |
|---|---|---|
| GB | 1059311 A | 2/1967 |
| WO | 2013126287 A1 | 8/2013 |
| WO | 2016033294 A1 | 3/2016 |
| WO | 2019165223 A1 | 8/2019 |

* cited by examiner

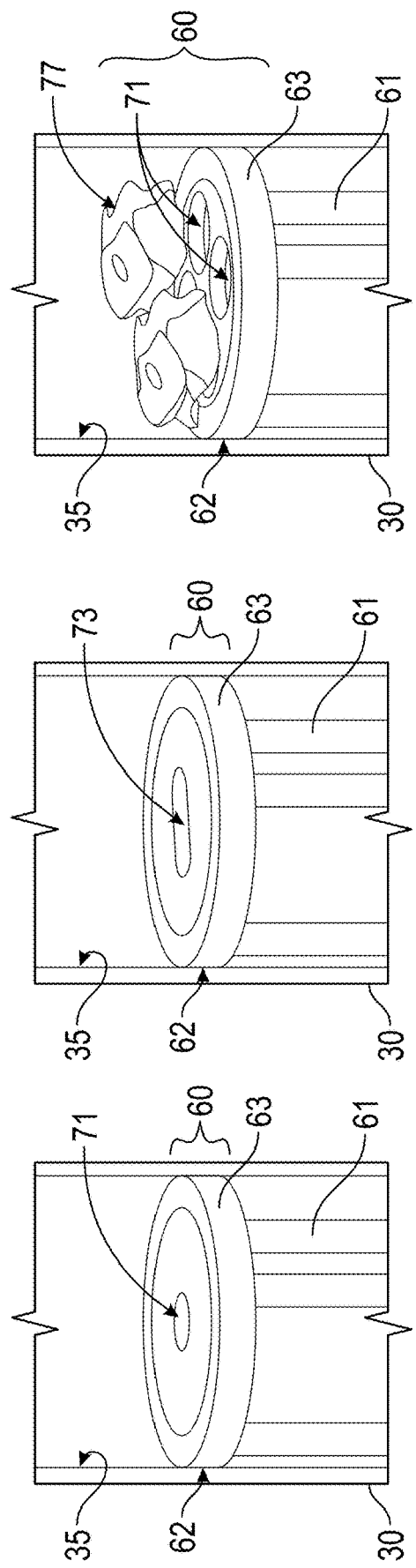

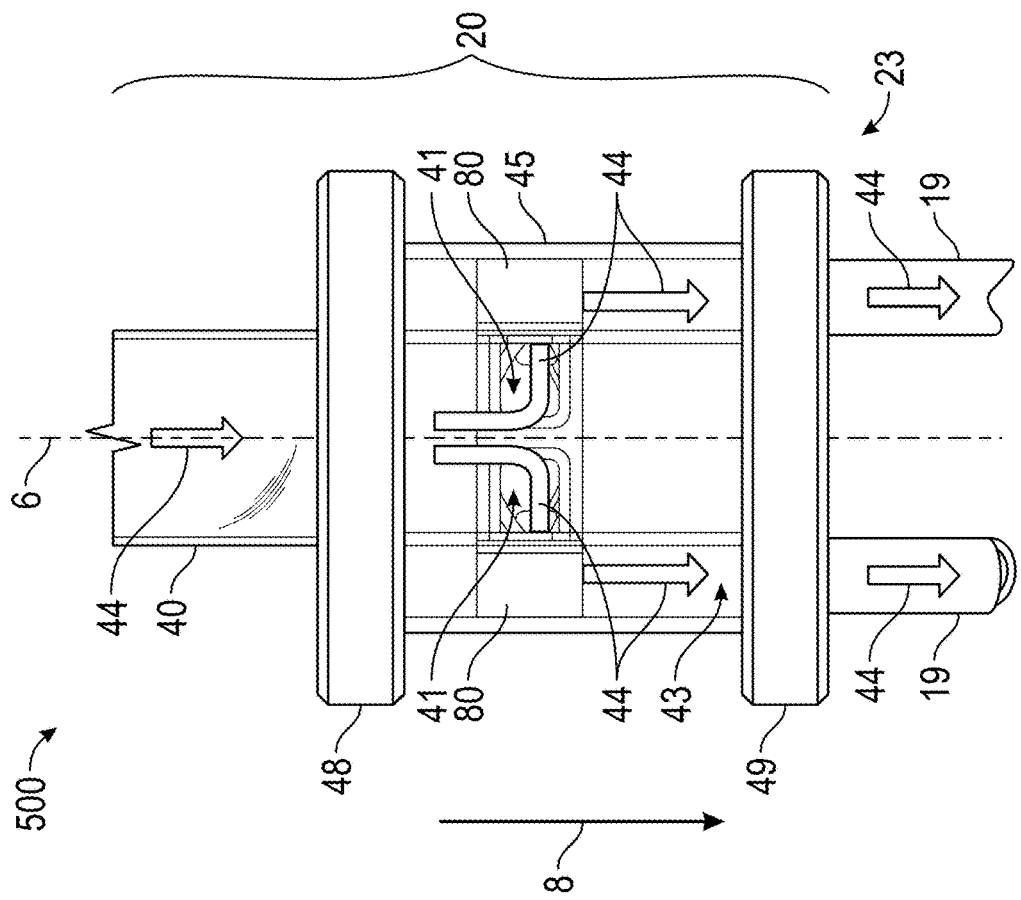
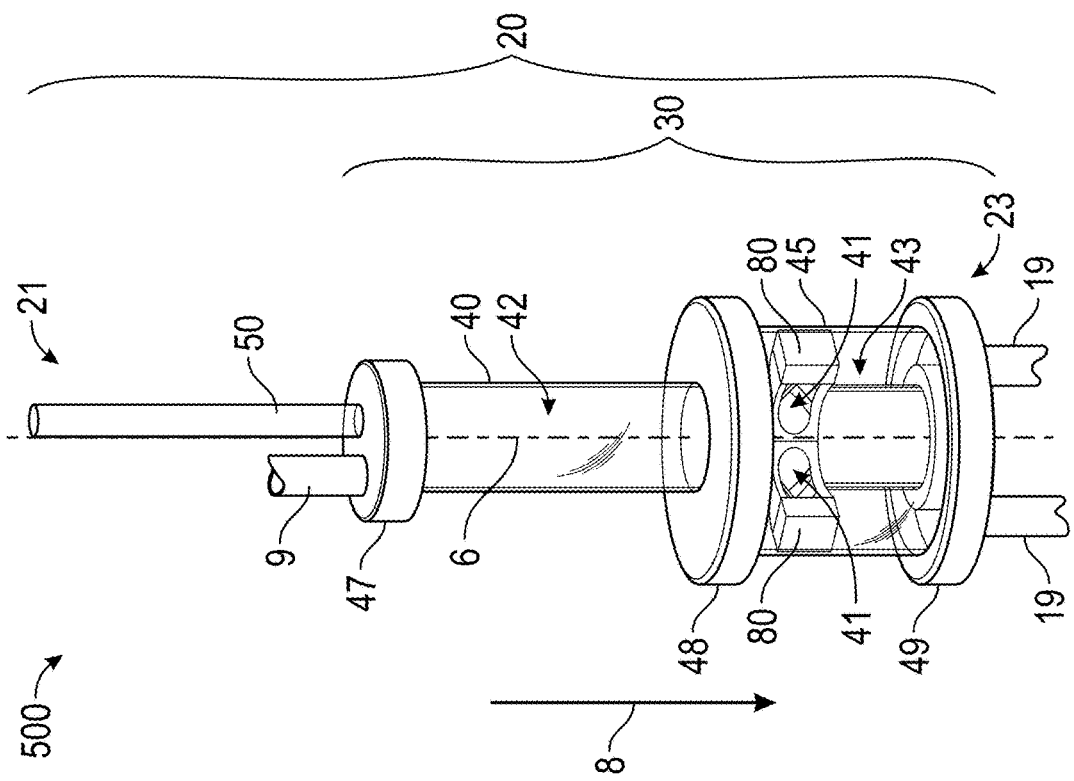
FIG. 5A
FIG. 5B

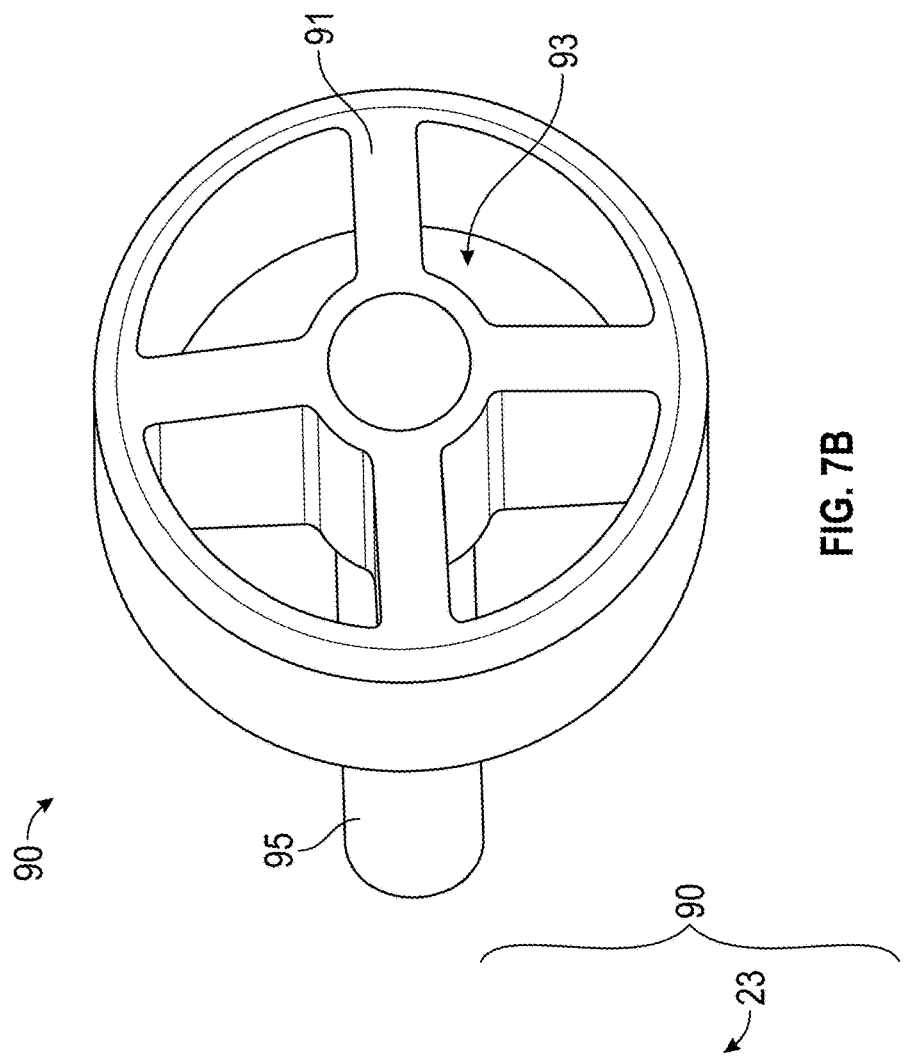
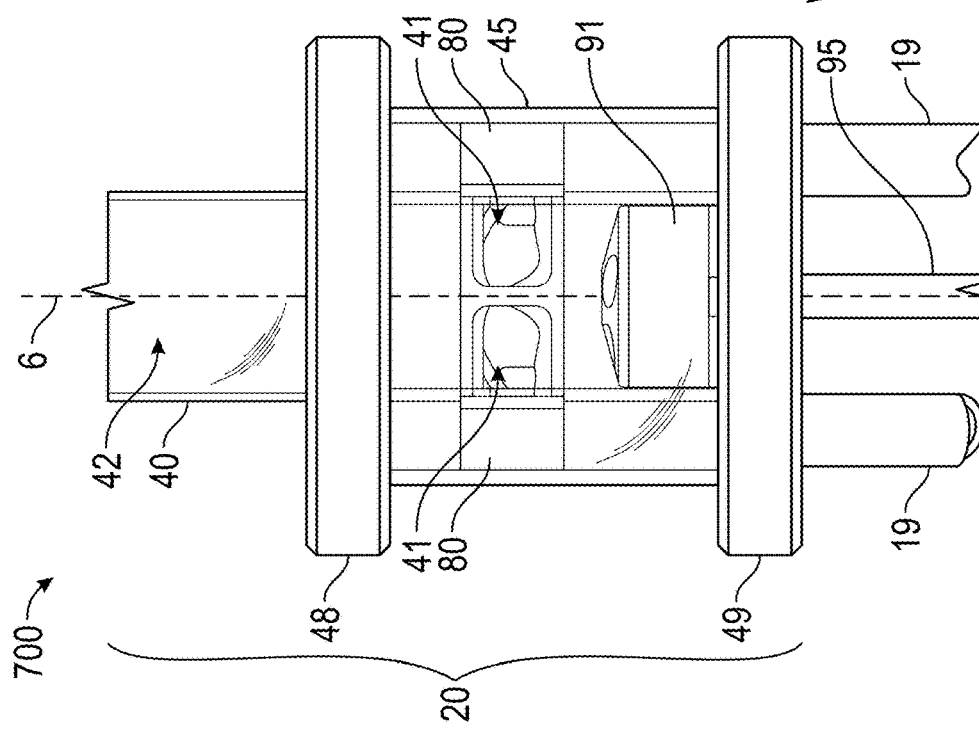

LOST CIRCULATION MATERIALS (LCM) AND LOST CIRCULATION SHAPES (LCS) TEST FIXTURE

CROSS-REFERENCE TO RELATED APPLICATIONS

This Application claims priority from U.S. Patent Application No. 62/976,033, filed Feb. 13, 2020, the contents of which are incorporated by reference in their entirety.

BACKGROUND

Field

The disclosure relates generally to subterranean operations and, more particularly, to apparatus and methods for simulation of subterranean environments.

Background Art

In wellbore drilling, a drilling fluid (or drilling mud) is circulated from a surface of the wellbore to downhole through the drill string. The fluid exits through ports (or jets) in the drill bit. The fluid picks up cuttings and carries the cuttings up an annulus formed between an inner wall of the wellbore and an outer wall of the drill string. The fluid and the cuttings flow through the annulus to the surface, where the cuttings are separated from the fluid. At the surface, the fluid can be treated with chemicals and then pumped back into the wellbore through the drill string to repeat the process.

During the drilling of subterranean wells, such as subterranean wells used in hydrocarbon development operations, drilling mud and other fluids can be pumped into the well. In certain drilling operations, the wellbore of the subterranean well can pass through a zone that has induced or natural fractures, are cavernous, or otherwise have an increased permeability compared with solid rock. Such a zone is known as a lost circulation zone. In such a case, the drilling mud and other fluids that are pumped into the well can flow into the lost circulation zone and become irretrievable. Thus, lost circulation is a situation in which the flow of the drilling fluid up the annulus toward the surface is reduced or is absent.

When unacceptable drilling fluid losses are encountered, lost circulation materials (LCM) are introduced into the drilling fluid from the surface. The revised fluid that includes the lost circulation materials is pumped downhole as part of the standard well circulation system. The revised fluid passes through a circulation port to plug and pressure seal the exposed formation at the point where losses are occurring. Once sealing has occurred and acceptable fluid loss control is established, drilling operations can resume.

Different types of traditional and specially designed loss control materials, slurries, and pills are used to control different lost circulation events. Loss circulation materials may generally be classified into several categories, including: surface plastering and shallow plugging materials; fracture sealing and deeper plugging materials; loss control slurry; interstitial bridging; and pore plugging materials. Such LCM are used to mitigate the lost circulation by blocking the flow path of the drilling mud into the formation. The type of LCM used in a lost circulation situation depends on the extent of lost circulation and the type of formation. Some traditional, solid materials typically used as LCM include, but are not limited to, wood fiber, popped popcorn, straw, bark chips, ground cork, mica, and ground and sized minerals.

SUMMARY

A testing apparatus for testing a fluid and a loss control material (LCM) is provided. In some embodiments, the testing apparatus comprises a testing chamber having an upstream end, a downstream end, a device central axis, and a general flow direction. The testing chamber includes a chamber body having an upstream cap, a downstream cap, a first chamber wall, and a second chamber wall. The first chamber wall has a first diameter and in part defines a first chamber interior, the second chamber wall has a second diameter, the first diameter is less than the second diameter, and both the first chamber wall and the second chamber wall are positioned relative to one another such that an annulus is defined in part in between. The upstream cap is proximate to and couples with at least the first chamber wall towards the upstream end. The downstream cap is proximate to and couples with at least the first chamber wall towards the downstream end. The first chamber wall defines a flow passage such that both a fluid and a lost circulation materials (LCM) may pass from the first chamber interior into the annulus. The chamber body further defines a chamber interior, which includes the annulus and the first chamber interior, through which the fluid and the LCM may traverse along a fluid flow path that is at least in part aligned with the general flow direction and the device central axis. The traversal of the fluid and the LCM along the fluid flow path is restricted by a flow restriction. The testing apparatus further includes a fluid inlet conduit that is in fluid communication with the first chamber interior and is configured to introduce fluid into the first chamber interior upstream of the flow passage, and a fluid outlet conduit that is in fluid communication with the annulus and is configured for passing both fluid and LCM from the annulus downstream of the flow passage.

In some embodiments, the flow passage may be configured to serve as the flow restriction.

In some embodiments, the fluid flow path through the flow passage may not be aligned with either the device central axis or the general flow direction.

Some embodiments of the testing chamber may further comprise an LCM inlet that is in fluid communication with the chamber interior and is configured to introduce LCM into the first chamber interior and upstream of the flow passage.

Some embodiments of the testing chamber may further comprise an orifice body, where the orifice body is configured to serve as the flow restriction, is positioned within the chamber body, and is coupled to the first chamber wall such that the fluid and the LCM must pass through the flow restriction.

In some embodiments, the orifice body may be configured to simulate a natural geologic formation.

In some embodiments, the orifice body may comprise an orifice inlet and an orifice outlet that are not collinear.

In some embodiments, the orifice body may comprise a plurality of orifice outlets.

In some embodiments, the orifice body may comprise a lateral orifice.

In some embodiments, the lateral orifice may be positioned within the annulus such that the orifice inlet is aligned with the flow passage.

In some embodiments, the fluid flow path through the lateral orifice may not be aligned with either the device central axis or the general flow direction.

In some embodiments, the lateral orifice may be configured with an outlet window opposite the orifice inlet.

Some embodiments of the testing apparatus may further comprise an integrity wiper comprising an agitation component coupled to a shaft, where the agitation component of the integrity wiper is positioned within the first chamber interior, where the downstream cap frictionally couples to the shaft to create both a fluid seal and to permit movement of the integrity wiper both axially along the device central axis and rotationally, and where the shaft has a length such that the agitation component of the integrity wiper may axially relocate between upstream and downstream of the flow passage.

A method of testing a lost control material (LCM) in a testing apparatus is provided. Some embodiments of the method may include: introducing a fluid into the testing apparatus such that the fluid has a first fluid flow rate as the fluid traverses a testing chamber of the testing apparatus along a fluid flow path, where the testing chamber comprises a flow restriction that restricts the traversal of the fluid and the LCM along the fluid flow path. Further, the method may include introducing the LCM into the testing apparatus such that the LCM traverses the fluid flow path along with the fluid, and determining a second fluid flow rate of the fluid traversing the fluid flow path after introduction of the LCM.

Some embodiments of the method may further include inducing a motion in the fluid proximate to a flow passage using an integrity wiper. The chamber body further comprises a first chamber wall, where the first chamber wall defines both the first chamber interior and the flow passage. The integrity wiper comprises an agitation component coupled to a shaft, where the agitation component of the integrity wiper is positioned within the first chamber interior and the shaft has a length such that the agitation component of the integrity wiper may axially relocate between upstream and downstream of the flow passage.

A testing system for testing a fluid and a loss control material (LCM) is provided. In some embodiments, the testing system comprises a testing apparatus comprising a testing chamber having an upstream end, a downstream end, a device central axis, and a general flow direction. The testing chamber includes a chamber body having an upstream cap, a downstream cap, a first chamber wall, and a second chamber wall. The first chamber wall has a first diameter and in part defines a first chamber interior, the second chamber wall has a second diameter, the first diameter is less than the second diameter, and both the first chamber wall and the second chamber wall are positioned relative to one another such that an annulus is defined in part in between. The upstream cap is proximate to and couples with at least the first chamber wall towards the upstream end. The downstream cap is proximate to and couples with at least the first chamber wall towards the downstream end. The first chamber wall defines a flow passage such that both a fluid and a lost circulation materials (LCM) may pass from the first chamber interior into the annulus. The chamber body further defines a chamber interior, which includes the annulus and the first chamber interior, through which the fluid and the LCM may traverse along a fluid flow path that is at least in part aligned with the general flow direction and the device central axis. The traversal of the fluid and the LCM along the fluid flow path is restricted by a flow restriction. The testing apparatus further includes a fluid inlet conduit that is in fluid communication with the first chamber interior and is configured to introduce fluid into the first chamber interior upstream of the flow passage, and a fluid outlet conduit that is in fluid communication with the annulus and is configured for passing both fluid and LCM from the annulus downstream of the flow passage. The testing system further comprises a test fluid reservoir fluidly coupled upstream of the testing chamber via the fluid inlet conduit, a test fluid collector fluidly coupled downstream of the testing chamber via the fluid outlet conduit, and a test fluid return conduit fluidly coupling test fluid collector to testing fluid reservoir.

In some embodiments, a fluid feed conduit fluidly couples to the testing apparatus via the fluid inlet conduit and a fluid exit conduit fluidly couples to the testing apparatus via the fluid outlet conduit.

In some embodiments, the test fluid reservoir further comprises a first test fluid reservoir and a second test fluid reservoir, where the test fluid collector further comprises a first test fluid collector and a second test fluid collector, and where the test fluid return conduit further comprises a first test fluid return conduit and a second test fluid return conduit, where the first test fluid return conduit fluidly couples the first test fluid reservoir to the first test fluid collector, and where the second test fluid return conduit fluidly couples the second test fluid reservoir to the second test fluid collector.

In some embodiments, the testing system is configured for an operating volumetric fluid flow rate in a range of from about 0 to about 4,000 liters per minute (L/min).

In some embodiments, the testing system is configured for an operating pressure in a range of from about 0 to about 2,500 pounds per square inch (psi).

In some embodiments, the testing apparatus may include a testing chamber having an upstream end, a downstream end, a device central axis, and a general flow direction.

The testing apparatus includes a chamber body having an upstream cap, a downstream cap, and a chamber wall. The chamber wall has a diameter and in part defines a chamber interior. The upstream cap is proximate to and couples with the chamber wall towards the upstream end and the downstream cap is proximate to and couples with at least the chamber wall towards the downstream end. The chamber body further defines a chamber interior, which includes the chamber interior, through which the fluid and the LCM may traverse along a fluid flow path that is at least in part aligned with the general flow direction and the device central axis. The testing chamber also includes an orifice body, where the orifice body is positioned within and coupled to the chamber interior such that the fluid and the LCM may not bypass the orifice body, and is configured to restrict the traversal of the fluid and the LCM from the upstream end towards the downstream end. The traversal of the fluid and the LCM along the fluid flow path is restricted by a flow restriction. The testing apparatus also includes a fluid inlet conduit that is in fluid communication with the chamber interior and is configured to introduce fluid into the chamber interior upstream of the flow restriction and a fluid outlet conduit that is in fluid communication with the annulus and is configured for passing both fluid and LCM from the chamber interior downstream of the flow restriction.

In some embodiments, the testing chamber may also include a lost circulation materials (LCM) inlet that is in fluid communication with the chamber interior and is configured to introduce LCM into the chamber interior upstream of the orifice body.

In some embodiments, at least one surface of the chamber body may be transparent.

In some embodiments, the orifice body may comprise an orifice plate perforated by at least one of a hole, a slot, a crack, or an irregular aperture.

In some embodiments, the orifice body may comprise an artificial formation plug perforated by least one pore.

In some embodiments, the at least one pore is shaped to simulate a natural geologic formation.

Other aspects and advantages provided in the detailed description of specific embodiments of the present disclosure will be apparent from the following description and the appended claims.

BRIEF DESCRIPTION OF DRAWINGS

FIGS. 3A-3C depict embodiments of an orifice body in the form of a plate according to one or more embodiments.

FIGS. 5A and 5B depict two views of an LCM testing apparatus with a first and second chamber wall according to one or more embodiments.

FIGS. 7A and 7B depict an integrity wiper according to one or more embodiments.

Throughout the figures, similar numbers are typically used for similar components.

Figure 1:
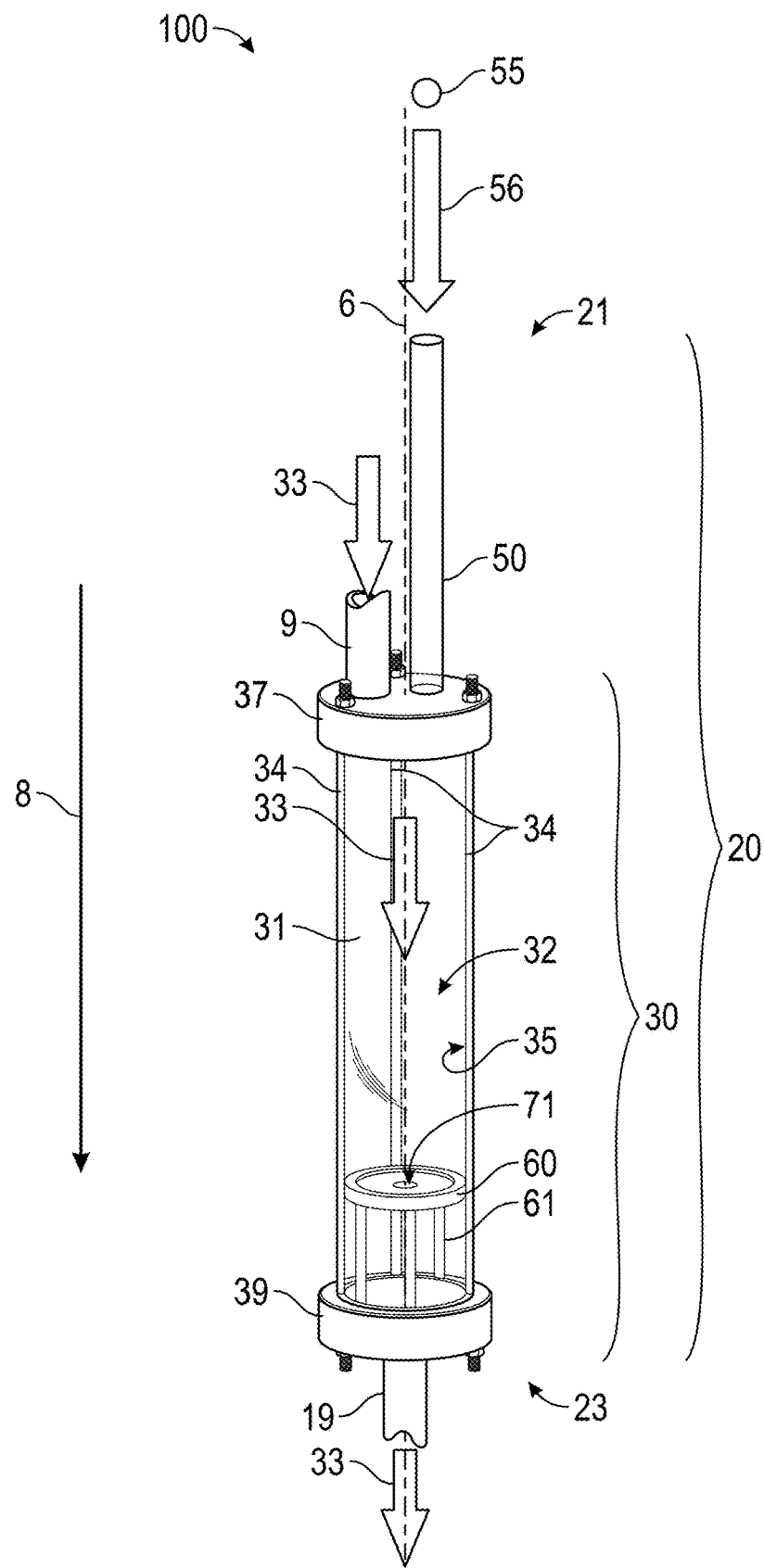
FIG. 1 depicts an LCM testing apparatus according to one or more embodiments.

In the figures, down is toward or at the bottom and up is toward or at the top of the figure. "Up" and "down" are generally oriented relative to a local vertical direction. However, as used throughout this disclosure, the terms "upstream" and "downstream" may refer to a position relative to the general direction of process or fluid flow, with upstream indicating a direction or position closer to start of the process and downstream referring to the direction or position closer to the end of the process. One of ordinary skill in the art understands that an object or a process may be upstream or downstream of another object or process while having no general relation to the position relative to vertical orientation unless otherwise specifically stated.

DETAILED DESCRIPTION

Field testing of materials for introduction into a wellbore is prohibitively time consuming and may create unforeseen hazards to personnel and equipment. Accordingly, there exists a continuing need for systems and methods of testing, using, and optimizing both drilling fluids and fluid loss control materials. Drilling fluids and fluid lost circulation materials (LCMs) should be tested both separately and together in simulated conditions of real-world situations to better appreciate their interaction.

Consequently, there exists a need for reproducible test- and laboratory-scale equipment that can effectively mimic such lost circulation situations so that lost circulation materials and lost circulation material blends can be evaluated prior to deployment in real-world situations, such as in a borehole or wellbore during exploration for or production of subterranean fluids.

It is desirable to be able to test the performance of different LCM under controlled yet realistic conditions. Accordingly, it is desirable to provide a device to simulate different characteristics of the subterranean formation of interest and to monitor the performance of LCM under these regulated, simulated conditions.

Existing LCM testing equipment involves constricting a fluid flowing vertically through some sort of orifice that is placed directly within the flow. This is in contrast with the geometry of many real-world lost circulation zones. Specifically, a lost circulation zone typically extends radially from the borehole central axis instead of being axially aligned either with the borehole or the general motion of the drilling fluid. Furthermore, when a borehole experiences a lost circulation event, the borehole extends in a first direction and the region of increased porosity extends out from the borehole in a second direction. Modern drilling may be based upon a vertical borehole, a horizontal borehole, or a deviated borehole. Furthermore, since the area of increased porosity may extend in any direction from the borehole, the angle between the first direction and the second direction may have any value from 0° to approaching 180° relative to one another. Existing LCM testing equipment fails to simulate the change in flow direction either at an orifice or at a real lost circulation zone.

Finally, in the real world, lost circulation events are caused by natural rock formations, such as pores, fractures, vugs, crevices, and fractures with irregular shapes and sizes. However, existing LCM testing equipment often includes flow restrictions with regular geometries (for example, circular holes or straight slits). Such regular geometry does not accurately simulate the irregular shapes of geological formations associated with lost circulation events.

Figure 12:
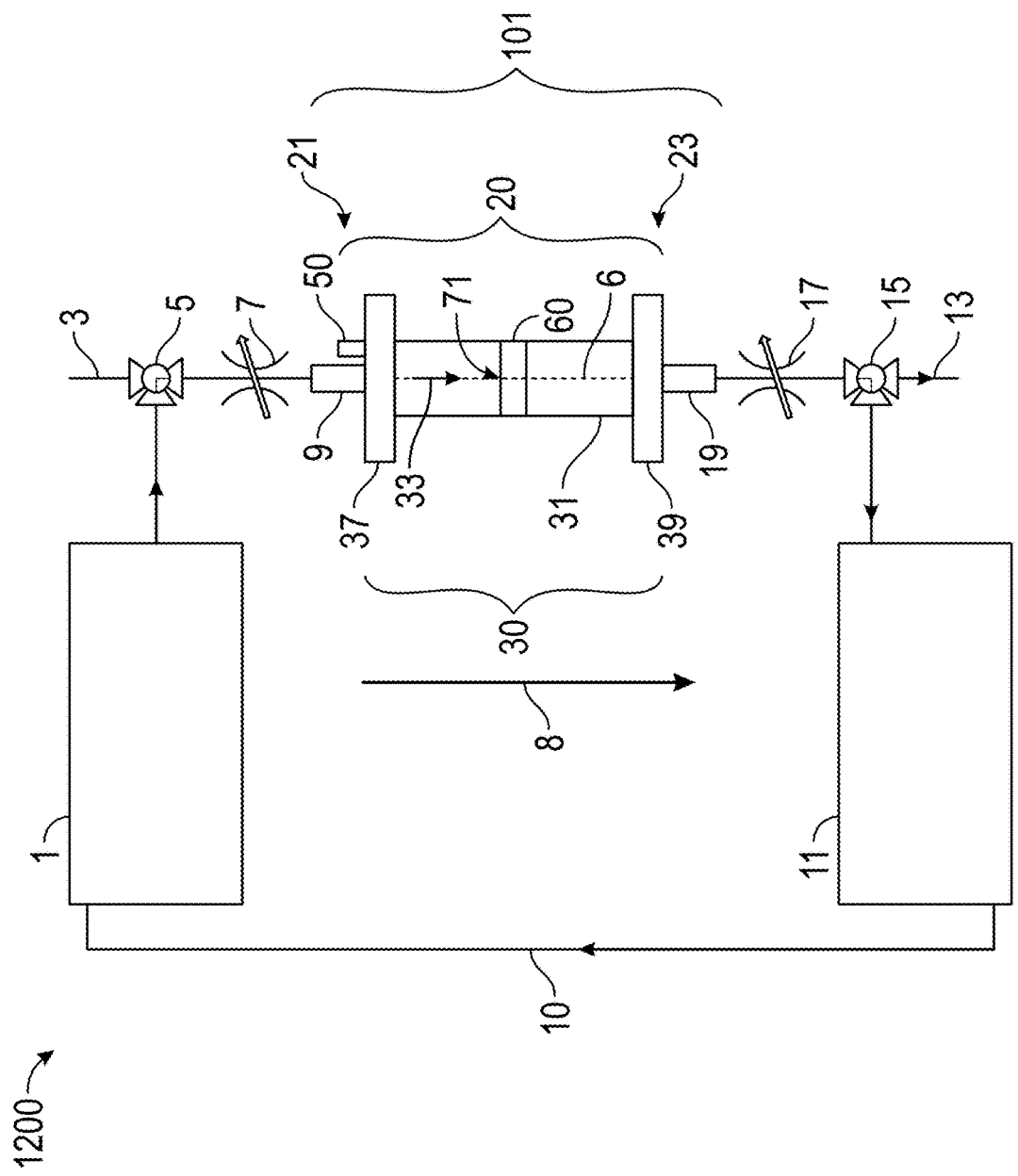
FIG. 12 depicts an LCM testing system according to one or more embodiments.
Figure 13:
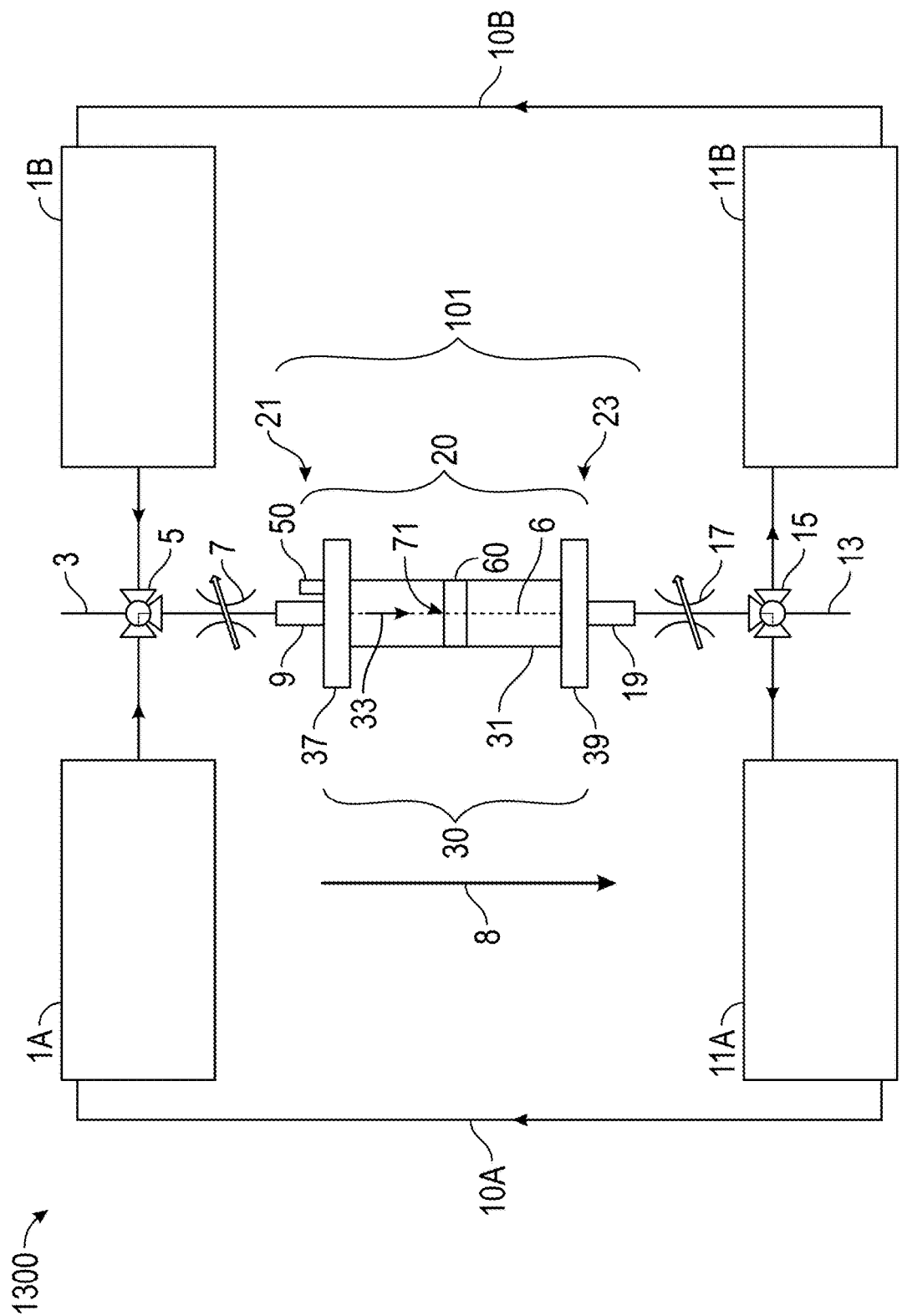
FIG. 13 depicts an LCM testing system according to one or more embodiments.

It may be a goal when deploying an LCM in a lost fluid zone to completely clog whatever perforations are encountered. However, one may want to study the behavior of LCM in a laboratory setting or in a controlled full-scale experimental setting prior to deployment in the field. As will be provided, one or more embodiments include a testing apparatus configured to test the interaction between LCM and some type of flow restriction that may simulate real-world perforations. Furthermore, such a testing apparatus may be incorporated into embodiments of a testing system, as depicted in FIGS. 12 and 13 and described in a forthcoming section. Finally, one or more embodiments of a method for testing an LCM in such a testing apparatus or testing system is described in a forthcoming section.

The testing apparatus and testing system disclosed and their methods of use alleviate these issues and improve the accuracy of testing LCM and fluids used with them.

FIG. 1 depicts an LCM testing apparatus according to one or more embodiments. FIG. 1 depicts testing apparatus 100 in relation to a device central axis 6 (dashed centralized line) and a general fluid flow direction 8 (arrow).

Testing apparatus 100 includes a testing chamber 20 having an upstream end 21 and a downstream end 23. Testing chamber 20 includes a chamber body 30 having an upstream cap 37, a downstream cap 39, and a chamber wall 31. Chamber body 30 (thus, together, upstream cap 37, downstream cap 39, and chamber wall 31) defines chamber interior 32.

Testing apparatus 100 also includes a fluid inlet conduit 9 and a fluid outlet conduit 19. Fluid inlet conduit 9 is disposed proximate upstream end 21 of testing chamber 20 and permits the introduction of a fluid into chamber interior 32. Fluid outlet conduit 19 is disposed proximate downstream end 23 of testing chamber 20 and permits passing of a fluid from chamber interior 32.

A fluid flow path is shown in part by arrows 33. The fluid flow path and arrows 33 showing parts thereof are aligned with the general flow direction 8. The fluid flow path and arrows 33 showing parts thereof is passing through testing apparatus 100 as going into fluid inlet conduit 9, aligned with the device central axis 6 through chamber interior 32, and out fluid outlet conduit 19.

In addition to chamber body 30, testing chamber 20 includes an orifice body 60. Orifice body 60 defines a hole 71 that serves as a flow restriction configured to restrict the traversal of the fluid and the LCM along the fluid flow path.

Finally, testing chamber 20 depicted in FIG. 1 includes an LCM inlet 50. An arrow 56 also depicts LCM 55 passing into LCM inlet 50. LCM 55 as shown in FIG. 1 is spherical, however, the LCM may be solid(s) having any regular or irregular geometric shape or may be liquid(s).

"Fluid" may be understood to mean any substance used to test the LCM that flows because it has no fixed shape. Thus, fluids may include liquids, gases, slurries, colloids, sols, and suspensions. The fluid may be similar to those used in the downhole environment. One or more embodiments may employ a fluid that contains a liquid, for example, water, crude oil, and combinations thereof. Further, the fluid may be a liquid with suspended or dissolved solids, for example, low specific gravity solids (for example, drill solids and bentonite), high specific gravity solids (for example, barite and hematite), or both. Some embodiments may employ a fluid that includes drilling mud or simulated drilling mud. The fluid may further include one or more additives, such as thickeners, deflocculants, lubricants, shale inhibitors, fluid loss additives, and weighting agents, beyond the LCM itself. Furthermore, the fluid may include one or more LCM at part of a treatment slurry.

In one or more embodiments, each LCM may include solvent(s) (for example, water or crude oil), solid(s) (for example, granular materials, powders, or colloidal particles), solutes (for example, polymer monomers), or a combination thereof. Thus, LCM may take the form of a solid, such as a granular material, a liquid, a solution, a slurry, a colloid, a sol, a suspension, or another related substance. Further, a treatment slurry containing the LCM may be formed prior to introduction into the testing apparatus.

In general physical terms, the testing apparatus may be described as having a "device central axis" that passes through a central portion of the device along a longitudinal line from its upstream end to its downstream end. For example, for testing apparatus 100 the device central axis 6 is shown as a dashed centralized line passing through the center of both upstream cap 37 and downstream cap 39. The device central axis may be useful in describing the relative position of or movement of objects or fluids within the testing apparatus.

In general fluid flow terms, the testing apparatus may be described as having a "general fluid flow direction" that describes the predominant fluid flow direction through the testing apparatus as the fluid moves from the upstream end to the downstream end. For example, for testing apparatus 100, the general fluid flow direction 8 may be described as vertical or "substantially" vertical as testing apparatus 100 is shown in FIG. 1 to be vertical or substantially vertical. The fluid flows from fluid inlet conduit 9, through chamber interior 23, and to fluid outlet conduit 19, in a vertical or substantially vertical manner. The general fluid flow direction may be useful in describing the relative movement of objects or fluids within the testing apparatus versus the predominant movement of fluid flow through the testing apparatus.

As discussed further, any number of additional components and systems may be incorporated upstream of fluid inlet conduit and downstream of fluid outlet conduit as part of a testing system as be discussed in greater detail in a forthcoming section.

In one or more embodiments, chamber body may have any regular geometric shape, such as cylindrical, cubic, triangular prismatic, cuboidal, rectangular prismatic, hexagonal prismatic, or prismatic. While the shape of chamber body is not limited, chamber body 30 as depicted in FIG. 1 is approximately cylindrical in nature. As shown, chamber body 30 has three surfaces: upstream cap 37 near upstream end 21; downstream cap 39 near downstream end 23; and chamber wall 31 (having an interior surface 35), which is curved and radially defines chamber body 30 and its enclosed chamber interior 32. Fluid inlet conduit 9 and LCM inlet 50 fluidly couple to upstream cap 37 and fluid outlet conduit 19 fluidly couples to downstream cap 39, permitting fluid and LCM to co-mingle in chamber interior 32.

Some embodiments of the testing apparatus may be sized appropriately for lab-bench scale testing. One or more embodiments of the chamber body may have an internal diameter on the order of 100 millimeters (mm) and a height on the order of 1000 mm. Additionally, the chamber body may also be scaled up to simulate actual well bore sizes, specifically the diameters and the axial lengths of the lost circulation zones of wellbores. One or more embodiment of chamber body may have an inner diameter of approximately 300 mm (millimeters) (~12 inches (in.)) and a length on the order of 3 meters. Such a large-scale chamber body may be appropriate for flow rates as will be described.

In one or more embodiments, the testing chamber may be cylindrical to more closely model the actual shape of a field borehole or wellbore. In such embodiments, the testing chamber may have a chamber body with a diameter that is similar to or the same as a diameter of a wellbore or borehole in the field. In such embodiments, wellbore equipment and LCM that is intended to be used in a field borehole may be "pre-tested" with a testing chamber having similar dimensions and under similar conditions. In some embodiments, testing chamber may have a chamber body with a diameter that is in a known arithmetic ratio of a wellbore or borehole in the field. Furthermore, a cylindrical testing chamber may provide additional flexibility for a number of factors, such as test apparatus design, manufacture, physical modification, condition simulation, and interchangeability (of aspects, including materials and sizes).

FIG. 1 shows that the fluid may enter testing chamber 20 via fluid inlet conduit 9, flow along the fluid flow path along arrows 33 within chamber interior 32, through hole 71 in orifice body 60, and exit through fluid outlet conduit 19. In one or more embodiments, the fluid flow path through testing chamber may be approximately vertical; however, other orientations, such as substantially vertical, deviated, substantially horizontal or horizontal, are envisioned. Further, the fluid flow path through testing chamber may be substantially straight and undeviating, meaning the fluid flow may proceed without significant diversion from parallel with the device central axis through the testing chamber. Additionally, the fluid flow path through the testing chamber passes through a hole in the orifice body, which serves as a flow restriction. This flow restriction is configured to restrict the traversal of the fluid and the LCM along the fluid flow path.

One or more embodiments of the chamber body may employ a modular design, such as a chamber wall, an upstream cap, and a downstream cap, that are all configured to couple to form the chamber body. The upstream cap and the downstream cap may be secured on either end of the chamber wall, such as using tie bars 34 as shown in FIG. 1, to form the chamber body in some embodiments. Such a modular design configuration may allow for ease of assembly and disassembly of chamber body. The modular configuration may facilitate various maintenance procedures, such as changing orifice bodies, clearing of chamber body following a test, or modifying chamber body via interchangeable components.

In embodiments, the testing chamber may be partially or fully transparent. "Transparent" may mean optically transparent, such as permitting visible light to pass in and out of the testing chamber, as well as transparent to non-visible electromagnetic (EM) wavelengths, such as ultraviolet, infrared, or X-ray frequencies. In one or more embodiments, one or more components of the testing chamber, including the chamber body (for example, the chamber wall, the upstream cap, or the downstream cap) and the orifice body, may be partially or fully transparent. In one or more embodiments, any transparent component or region may be formed of materials that support transparency, such as, but not limited to, glassy or polymeric materials, or a combination thereof. These transparent component or region of the testing chamber may allow visual monitoring as well as optical or EM-based measurements of the fluid, the LCM, or both, during a test.

In some other embodiments, the testing chamber may be partially or fully opaque. In one or more embodiments, one or more components of the testing chamber, including the chamber body (for example, the chamber wall, the upstream cap, or the downstream cap) and the orifice body, may be partially or fully opaque. In one or more embodiments, one or more components of the chamber body may be formed from one or more non-transparent materials (for example, steel, stainless steel, aluminum, titanium, or any alloys or composites of these metals). Given an inability to visually observe an ongoing test, test results in such a test may reflect alternative qualitative factors, such as the flow rate and the pressure detected, via sensors, as will be described further.

One or more embodiments of the testing apparatus may be used to test non-transparent drilling muds, such as under scaled-up (that is, closer to field) conditions. If a non-transparent test fluid is used, components of the testing chamber, such as the chamber body and the orifice body, may be made from non-transparent material (for example, steel).

In one or more embodiments, a combination of transparent and non-transparent materials may also comprise the testing chamber, including the chamber body and the orifice body. As an example, the upstream cap and the downstream cap may be made from non-transparent material(s) (for example, stainless steel) while the chamber wall and the orifice body may be fabricated from transparent material(s) (for example, glassy or polymeric materials). Other combinations of transparent and non-transparent materials will be readily understood to be encompassed in embodiments.

The choice of and combination of material(s) for the testing chamber may depend on a variety of factors, including but not limited to achievable pressure ratings, transparency, test fluid compatibility, and testing temperature. For example, although metals are opaque, a metallic test chamber may allow for testing to be performed at greater pressures and temperatures than a similarly-configured testing chamber formed from a polymeric material (although it is not assumed to be true in all instances of the embodiments).

FIG. 1 depicts LCM inlet 50, as previously described. An arrow 56 indicates introduction of LCM 55 into LCM inlet 50. In one or more embodiment, LCM inlet may be upstream of the orifice body to allow the LCM to flow and interact with the fluid through the chamber body, and to potentially clog the orifice body. One or more embodiments of the LCM inlet will be discussed in greater detail in forthcoming sections.

The orifice body, which defines the flow restriction, may be disposed in the chamber body to restrict the fluid flow through the chamber body. In FIG. 1, orifice body 60 (on top of an orifice stand 61) is shaped like a plate, such as a traditional round orifice plate, with a single, centralized hole 71 that serves as the flow restriction. In some embodiments, the orifice stand may support the orifice body within the chamber body. One or more embodiments of the orifice body will be discussed in greater detail in a forthcoming section.

In one or more embodiments, the orifice body may be fabricated from ceramic, polymeric, or metallic materials via additive or subtractive manufacturing processes. Here, "additive manufacturing" may be taken to mean any type of manufacturing process that builds a three-dimensional (3D) object from a computer-aided design model. Additive manufacture is also known as 3D printing.

Figure 2:
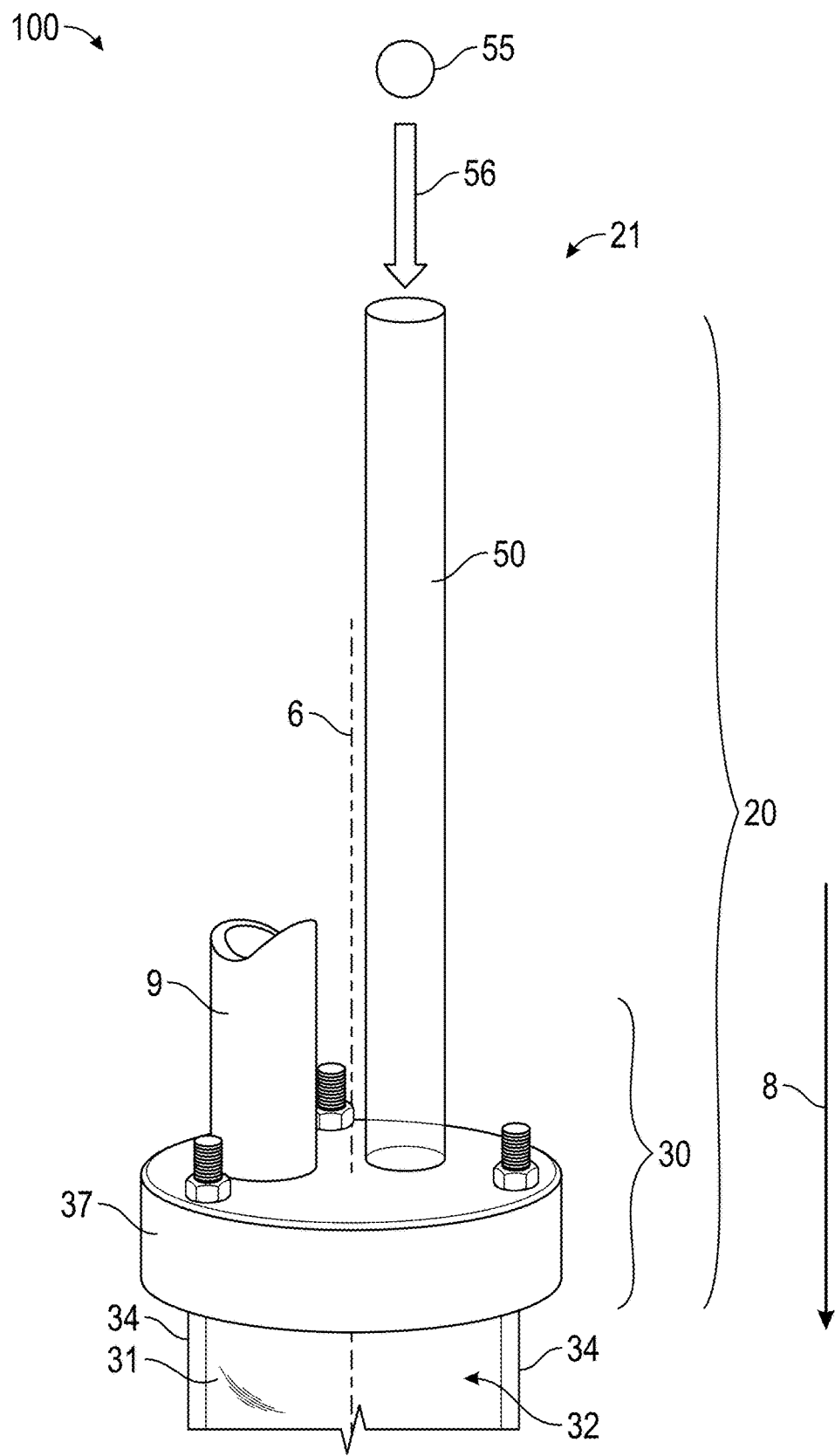
FIG. 2 depicts a view of an LCM inlet of an LCM testing apparatus according to one or more embodiments.

FIG. 2 depicts a view of an LCM inlet of a testing apparatus according to one or more embodiments. FIG. 2 depicts the area near an upstream end 21 of a testing chamber 20 to highlight an LCM inlet 50. LCM 55 is shown along with an arrow 56 indicating the path for introduction into chamber interior 32 via LCM inlet 50. FIG. 2 also shows a device central axis 6 (dashed centralized line) and a general fluid flow direction 8 (arrow).

One or more embodiments of LCM inlet may include either a valve at an upstream opening, a downstream opening, or both. One or more valves may be incorporated to prevent adverse occurrences, such as outside contamination or back flow of fluid from the chamber body into the LCM inlet.

LCM inlet 50 depicted in FIG. 2 is a long, cylindrical, hollow pipe. However, the configuration of the LCM inlet may take any form to permit LCM introduction. The LCM inlet may be sufficiently large for the LCM to traverse the LCM inlet and the upstream cap into the chamber body. The LCM inlet may also simply be an opening in the upstream cap (without any extension) and with or without a valve.

In some embodiments, the LCM inlet may be partially or fully transparent. As in the embodiment depicted in FIG. 2, the LCM inlet chamber body or components thereof (for example, the pipe or the valves) may be transparent or semi-transparent. In one or more embodiments, any transparent LCM inlet components may be formed of glassy or polymeric materials, or a combination thereof. These transparent component(s) may allow visual monitoring as well as optically based measurements of the LCM within the LCM inlet.

The LCM inlet may be used to introduce LCM into the test fluid flow within the chamber body. Introducing LCM via the LCM inlet may assist a user control the sequence and volume of one or multiple types of LCM as they are introduced. Further, the LCM inlet may allow for the observation of LCM interaction with a flow restriction that is already experiencing a flowing fluid. Finally, the LCM inlet may be used to introduce LCM that may be too large for component(s) upstream of the fluid inlet conduit and, thus, may form an undesired blockage upstream of the fluid inlet conduit.

FIGS. 3A-3C depict several orifice bodies according to one or more embodiments. FIGS. 3A-3C include three configurations of an orifice body 60 on an orifice stand 61 in a chamber body 30 of an embodiment of a testing apparatus (FIG. 1). Each orifice body 60 defines one or more flow restrictions that limit the fluid flow through chamber body 30. Each depicted orifice body 60 includes an orifice plate 63.

To successfully route fluid only along the intended flow path, the outer edge of the orifice plate may have a shape that is configured to correspond with the interior surface of the chamber body such that the fluid may not bypass the flow restriction(s). FIGS. 3A-3C, for example, an outer edge 62 of orifice plate 63 may frictionally or functionally couple with an interior surface 35 of chamber body 30. Another example is that any gap or space between the outer edge of the orifice plate and the interior surface of the chamber body may be sealed with an adhesive or another material that not only secures the orifice plate in position within the chamber body but also prevents fluid from bypassing the orifice of the orifice plate. A final example is that any gap or space between the outer edge of the orifice plate and the interior surface of the chamber body may be sealed with an additional component, such as a polymer, silicone, or metal gasket (not depicted), that prevents fluid bypass of the orifice plate. One having skill in the art will appreciate other methods to prevent fluid from traveling between the outer edge of the orifice plate and the interior surface of the chamber body, thereby bypassing the flow restriction(s) in the orifice plate.

FIG. 3A depicts orifice plate 63 on an orifice stand 61. Orifice body 60 restricts the fluid flow path through one flow restriction (hole 71) defined by orifice plate 63. Such an orifice plate in some embodiments may be perforated by one or more holes that serve as one or more flow restrictions. Such combinations of more than one flow restriction may have a pattern or may be randomly distributed on orifice plate. FIG. 3B depicts orifice plate 63 on orifice stand 61 where the fluid flow path is again restricted through one flow restriction (slot 73) defined by orifice plate 63. Such an orifice plate in some embodiments may be perforated by one or more slots. Such combinations of more than one flow restriction may have a pattern or may be randomly distributed on the orifice plate. An orifice plate may have flow restrictions with simple shapes, such as holes, slots, slits, crosses, and other combinations of geometric designs and patterns thereof, to permit comparison with prior-obtained data using similar configurations. FIG. 3C depicts orifice plate 63 on orifice stand 61 where orifice plate 63 defines several holes 71 (some of which are partially-obscured). In FIG. 3C, orifice body 60 also restricts the fluid flow path by obstructing the fluid flow path with a simulated rock pile 77. Such additional flow obstructions to traversing the orifice body may help simulate a tortuous fluid flow path, which may better simulate the fluid flow path experienced downhole by the LCM.

In some embodiments, the orifice plate may serve to support one or more flow obstruction, such as a simulated rock pile. For example, the perforation(s) in orifice plate 63, such as holes 71 depicted in FIG. 3C, may not significantly restrict the fluid flow path through chamber body 30. In such a case, the spacing between rocks within simulated rock pile 77 may not only form a torturous fluid flow path but also form a series of irregular flow restrictions through which the fluid flow path is restricted within orifice body 60. The restriction of the fluid flow path through an orifice body may be largely or solely due to the obstruction(s), such as in this case the simulated rock pile. The majority of the interaction of between the LCM and the orifice body in such a case may be with the simulated rock pile and not with perforations in the orifice plate. In some such embodiments, the orifice plate may be formed of a material such as mechanically robust, large-gauge mesh, to provide mechanical support to the simulated rock pile with minimal flow resistance.

The simulated rock pile may be compositionally artificial, that is, it may be fabricated using additive or subtractive manufacturing of metallic, ceramic, glassy, or polymeric materials, or combinations thereof. The simulated rock pile in some embodiments may be comprised of an arrangement of naturally-sourced geologic materials (for example, surface rocks or aggregated well bore cuttings).

In one or more embodiments, the orifice plate and the simulated rock pile may be formed from dissimilar materials. The orifice plate may be formed of a first material (for example, stainless steel or polycarbonate) while the simulated rock pile may be formed of a second material (for example, ceramic or natural rock). Other combinations of materials are envisioned. In one or more embodiments, the simulated rock pile and the orifice plate may be formed as a single component, such as with additive manufacturing. In one or more embodiments, the simulated rock pile may be permanently attached to the orifice plate, such as with welding, adhesive, or some other method known in the art. In one or more embodiments, the rocks within the simulated rock pile may be permanently attached to one another, such as with welding, adhesive, or some other method known in the art. In one or more embodiments, all rocks within the simulated rock pile may be formed as a single component, such as by additive or subtractive manufacturing.

In one or more embodiments, the orifice body or components thereof (for example, the orifice plate or the simulated rock pile) may be partially or fully transparent. A transparent orifice plate, simulated rock pile, or both, may each be comprised of glassy or polymeric materials, or a combination thereof. These transparent material(s) may allow visual monitoring of dual-phase (fluid and solid) flow through the flow restrictions defined by the simulated rock pile. In addition, transparent materials may permit the observation and memorialization of the interaction with and obstruction of the flow restriction(s) with LCM. Such observational data may permit a better understanding of the fluid and solids mechanics of interactions between LCM and the flow restriction(s), such as stacking, under both dynamic and steady-state fluid flow conditions.

An orifice body (or, specifically, an orifice plate) may have any thickness. The thickness may be measured along a line aligned with the device central axis. In some embodiments, the orifice body (or orifice plate) may have a thickness less than the diameter of the orifice body, which may be measured perpendicular to the device central axis (for example, a thickness less than 5% of the diameter, less than 10%, less than 25%, less than 50%, or less than 90%). In some other embodiments, the orifice body (or orifice plate) may not be plate-like but rather plug-like with a thickness equal to or greater than the diameter (for example, a thickness greater than 100% of the diameter, greater than 150%, greater than 200%, or greater than 500%).

Any shape, configuration, or number of flow restriction(s) may be present in the orifice body. These flow restriction(s) may take the form of perforation(s) in the orifice plate (as in FIGS. 3A and 3B), gap(s) between rocks in a simulated rock pile (as in FIG. 3C), or any other confirmation that restricts the fluid flow path. Further, the orifice body may include a mixture of flow restriction(s) conformations. The embodiments depicted in FIGS. 3A-3C and described here are only intended to illustrate a range of potential options to a person having skill in the art.

In some embodiments, the orifice body may include flow restriction(s) in the form of perforation(s) defined by the orifice plate. Any shape, configuration, or number of perforations may be present in the orifice plate. While not depicted in FIGS. 3A and 3B, the perforation(s) in orifice plate 63 may also take the shape of a crack, pore, irregular aperture, or any non-geometric shape, according to one or more embodiments. The size, shape, or both, of perforation(s) in the orifice plate may vary through the thickness of the orifice plate. An irregularly shaped perforation may be designed to closely simulate or to generally approximate a known or suspected rock porosity structure, fracture, or vug. See, for example, FIGS. 4A and 4B.

In one or more embodiments, the one or more flow restriction(s) may be smaller than the LCM to be tested. Thus, the LCM may not pass through the flow restriction(s), thereby forming an obstruction in the flow restriction(s) that blocks the flow of fluids through the orifice body. In one or more embodiments, the flow restriction(s) may be smaller than some of the LCM to be tested but larger than others. This may be the case if an introduced LCM has a range or distribution of sizes. In one or more embodiments, the flow restriction(s) may be slightly smaller than the largest LCM being tested. "Slightly smaller" may mean that the perforation(s) may be at least 10% smaller than the LCM (for example, 5% smaller, 2% smaller, or 1% smaller, and ranges in-between). In some embodiments, the orifice body may include flow restrictions having a range of sizes, confirmations, or both. In some embodiments, the LCM may be substantially smaller in size than the flow restriction(s). The focus of such a study may be to observe bridging behavior.

In one or more embodiments, the orifice body may be interchangeable. Interchangeable orifice bodies may increase the versatility of the testing apparatus, such that a single apparatus may be used to investigate the interaction between an LCM and more than one flow restriction geometry. Such flexibility also would permit the testing of different LCM systems with various geometries and sizes using a single apparatus.

Figure 4B:
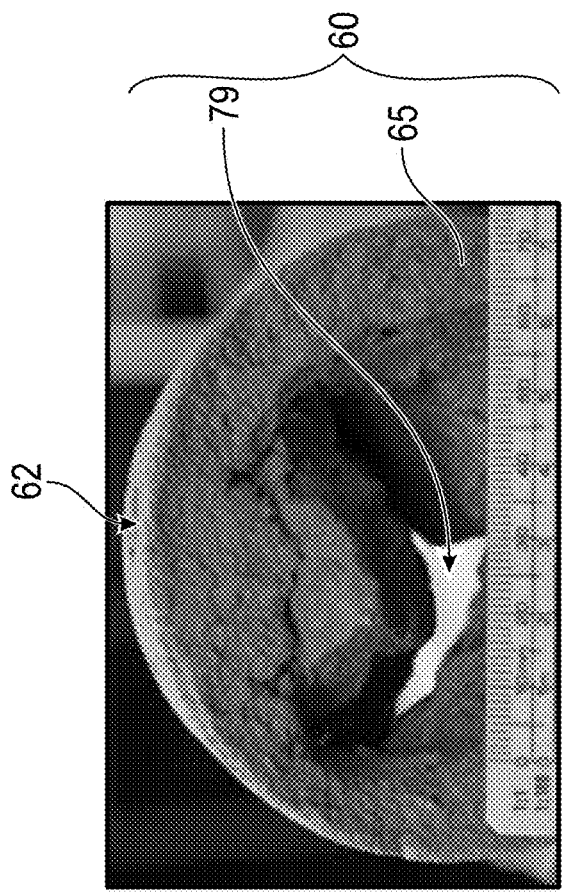
FIGS. 4A and 4B depict embodiments of an orifice body in the form of an artificial formation plug according to one or more embodiments.
Figure 4A:
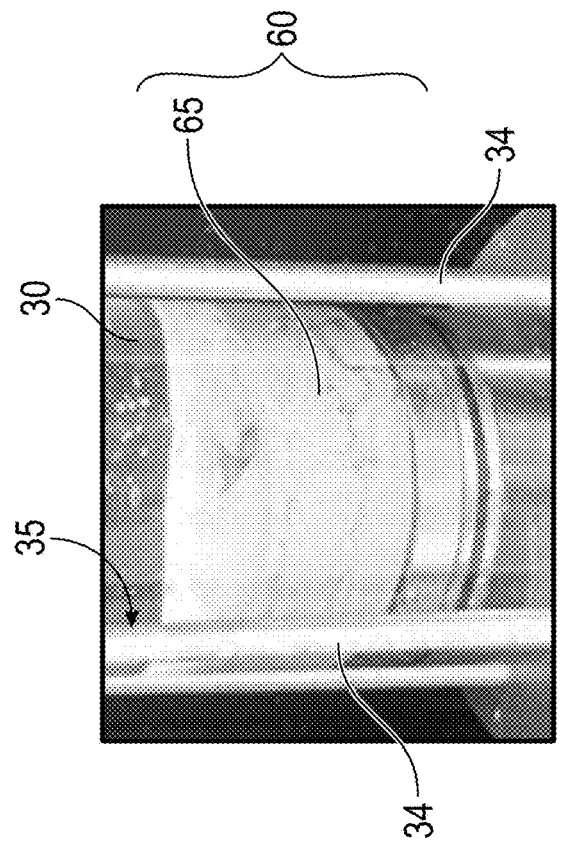

FIGS. 4A and 4B depict an orifice body in the form of an artificial formation plug according to one or more embodiments. FIGS. 4A and 4B depict two views of an orifice body 60 in the form of an artificial formation plug 65. FIG. 4A depicts artificial formation plug 65 within chamber body 30. FIG. 4B depicts artificial formation plug 65 in plan view so the flow restriction having the form of a pore 79 is visible.

Like the orifice plate (FIGS. 3A-3C), to successfully direct fluid only through one or more pores, the outer edge of the artificial formation plug may have a shape that is configured to correspond with the interior surface of chamber body such that the fluid does not bypass the one or more flow restriction(s), as previously described. Any gap or space between the outer edge of artificial formation plug and the interior surface of chamber body may be sealed with an adhesive or another material, as previously described. Any gap or space between the outer edge of orifice plate and the interior surface of chamber body may be sealed with an additional component, as previously described.

In some embodiments, the artificial formation plug may be thicker than an orifice plate as depicted in FIGS. 3A-3C. Such thickness may represent a greater volume and portion of the axial length of the chamber body to represent a realistic depth of a pore. Additionally, the artificial formation plug may be configured to more closely simulate a natural rock formation, such as by including flow restriction(s) having the form of an array of micropores, one or more wormholes, a single long fissure, a vug, or combinations thereof. As such, the artificial formation plug may be designed using a 3D scan or 3D rendering of a rock formation. The artificial formation plug may be fabricated via additive manufacturing or subtractive manufacturing. The artificial formation plug may be formed of metallic, ceramic, glassy, or polymeric materials, or a mixture thereof.

In some embodiments, the artificial formation plug may be partially or fully transparent. A transparent artificial formation plug has the same observational benefits as previously described. In fact, the benefit may actually be even greater if the artificial formation plug is configured from a known pore or vug in a wellbore because the behavior of mitigation methods and materials can be confirmed in the laboratory before implementation in the field.

In one or more embodiments, orifice bodies (including, orifice plates, simulated rock piles, or artificial formation plugs) may be interchangeable within a testing apparatus. Interchangeable orifice bodies may increase the flexibility of the testing apparatus. A single testing apparatus may be used to investigate the interaction between a single LCM and multiple orifice bodies geometries as well as the interaction between a single orifice bodies geometry and multiple LCMs. One having skill in the art will appreciate the variety of experimental studies that are enabled by a testing apparatus that readily accommodates interchangeable orifice bodies.

In one or more embodiments, the orifice body may be positioned away from both the upstream and the downstream ends of the chamber body. Such positioning of the orifice body may allow the fluid and dual-phase flow upstream and downstream of the orifice body to be visually observed. Such positioning of the orifice body may also allow the fluid and dual-phase flow within the orifice body to be more easily observed, for example, using a transparent orifice body.

Downhole, the fluid paths encountered in a lost circulation zone may be nonlinear and convoluted. Therefore, a more tortuous fluid path than one confined to a single chamber body, such as the one depicted in FIG. 1, may be studied.

FIGS. 5A and 5B depict two views of an LCM testing apparatus with a first and second chamber wall according to one or more embodiments. FIG. 5A shows a testing apparatus 500 having a testing chamber 20 with an upstream end 21 and a downstream end 23. Testing apparatus 500 also includes a fluid inlet conduit 9 and two fluid outlet conduits 19. Testing chamber 20 includes a chamber body 30, where chamber body 30 includes a first chamber wall 40, a second chamber wall 45, an upstream cap 47, a downstream cap 49, and a chamber connector 48. Testing chamber 20 also includes an LCM inlet 50 in upstream cap 47 near upstream end 21. FIGS. 5A and 5B also show a device central axis 6 (dashed centralized line) and a general fluid flow direction 8 (arrow).

FIG. 5B depicts a magnified view of the same testing apparatus 500, enlarged on downstream end 23 of testing chamber 20. Furthermore, a fluid flow path is shown in part by arrows 44 through testing chamber 20 and into fluid outlet conduits 19.

In the embodiment depicted in FIGS. 5A and 5B, both first chamber wall 40 and second chamber wall 45 are cylindrical, with second chamber wall 45 having a greater diameter than first chamber wall 40, where each diameter is measured perpendicular to device central axis 6. The second chamber wall may be roughly concentrically arranged around a portion of the first chamber wall. In such a configuration, an annulus is defined between the first chamber wall and the second chamber wall.

First chamber wall 40 is capped near upstream end 21 of testing chamber 20 by upstream cap 47. Fluid inlet conduit 9 and LCM inlet 50 are both separately coupled to upstream cap 47 and in fluid communication with a first chamber interior 42. Both first chamber wall 40 and second chamber wall 45 are capped near downstream end 23 of testing chamber 20 by downstream cap 49. Both fluid outlet conduits 19 are coupled to downstream cap 49 and in fluid communication with an annulus 43. Also, a portion of first chamber wall 40 is coupled to chamber connector 48 and is positioned in part within the interior of second chamber wall 45, as previously described. In such an embodiment of the testing chamber, the first and second chamber walls may have unequal lengths.

In some embodiments, multiple chamber walls may or may not have equal lengths. Some embodiments of the testing chamber may or may not include a chamber connecter. In some such embodiments, both the first and the second chamber walls may be capped near the upstream end by the upstream cap. In some such embodiments, both the first and the second chamber walls may be capped near the downstream end by the downstream cap. See, for example, FIGS. 9, 10, and 11.

One fluid inlet conduit is disposed at an upstream end of testing chamber. The fluid inlet conduit is coupled in the upstream cap. The fluid inlet conduit is configured to introduce fluid into the first chamber interior. In one or more embodiments, any number of fluid inlet conduits may be included in the testing apparatus.

The LCM inlet may be used to introduce LCM into the test fluid flow within the chamber body. Specifically, the LCM inlet may be used to introduce LCM into the first chamber interior. The LCM inlet may be upstream of an orifice body, such as the two lateral orifices 80 depicted in FIG. 5A.

The interior of the testing chamber includes two volumes: the first chamber interior and the annulus. The first chamber interior is enclosed between the upstream cap, the first chamber wall, and the downstream cap. In some embodiments, such as those having a chamber connector, the annulus may be enclosed between the downstream cap, the first chamber wall, the second chamber wall, and the chamber connector. In some embodiments, such as those lacking a chamber connector, the annulus may be enclosed between the downstream cap, the first chamber wall, the second chamber wall, and the upstream cap.

As shown in FIGS. 5A and 5B, first chamber wall 40 defines at least two flow passages 41 found in first chamber wall 40 toward downstream end 23 of testing chamber 20. Flow passages 41 are voids in the first chamber wall 40. Through flow passages 41 in first chamber wall 40, the volumes of chamber body 30 (first chamber interior 42; annulus 43) are in one-way fluid communication along a fluid flow path (arrows 44) from first chamber interior 42 to annulus 43. Any number of configurations of the flow passages may be defined by the first chamber wall.

As shown in FIGS. 5A and 5B, two fluid outlet conduits 19 are disposed near downstream end 23 of testing chamber 20. The fluid outlet conduits are configured to discharge fluid and LCM from the annulus. In one or more embodiments, any number of fluid outlet conduits may be included in the testing apparatus.

Fluid traversing the testing chamber may be introduced to the chamber body by the fluid inlet conduit, flow through the first chamber interior, through the flow passages, into the annulus, and then pass from the chamber body via the fluid outlet conduits.

In one or more embodiments, one or both of first chamber wall and second chamber wall may be fabricated from transparent or semi-transparent materials to allow measurement and observation of LCM within the fluid. Both first chamber wall 40 and second chamber wall 45 are shown as transparent in FIGS. 5A and 5B. When both the first chamber wall and the second chamber wall are transparent, most of the fluid path within the testing chamber may be visually observed, documented, and measured through optical and electromagnetic means.

As in the embodiment depicted in FIGS. 5A and 5B, the chamber body may be partially or fully transparent. In one or more embodiments, the chamber body or components thereof (for example, the first chamber wall, the second chamber wall, the upstream cap, the downstream cap, or the chamber connector) may be transparent or semi-transparent. In one or more embodiments, any transparent testing chamber components may be formed of glassy or polymeric materials, or a combination thereof. These transparent component(s) may allow visual monitoring as well as optically based measurements of the fluid, the LCM, or both, during a test.

Additionally, FIGS. 5A and 5B include two orifice bodies in the form of lateral orifices 80. Lateral orifices may serve to both modify the fluid flow path direction and define flow restrictions of the fluid flow path from the first chamber interior into the annulus. Lateral orifices 80 will be detailed in FIGS. 6A-6C and the accompanying description.

In one or more embodiments, any number or configuration of orifice bodies may be employed with the chamber body, including but not limited to the orifice bodies shown in FIGS. 3A-3C, 4A, 4B, and lateral orifices 80 of FIGS. 5A and 5B.

In one or more embodiments, the testing apparatus may be designed in a modular fashion so the testing chamber may be reconfigured with either a single chamber wall or with a first and second chamber walls, such as between the testing apparatus shown in FIG. 1 and the testing apparatus shown in 5A.

Figure 6C:
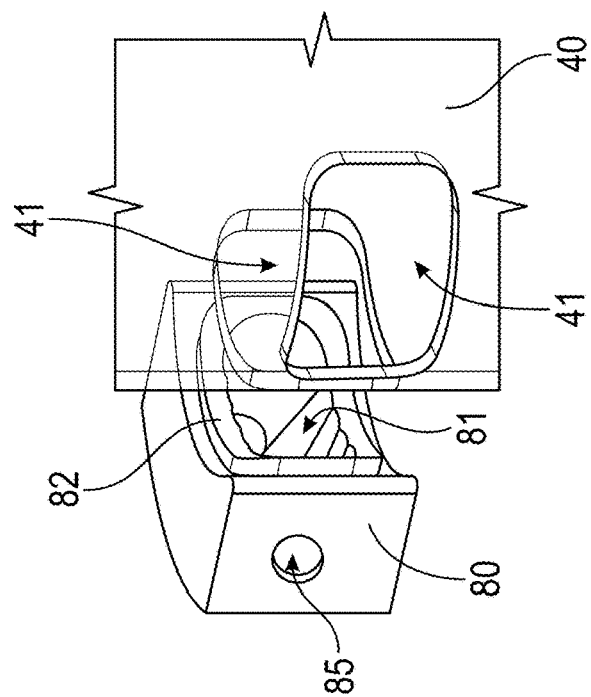
FIGS. 6A-6C depict views of a lateral orifice according to one or more embodiments.
Figure 6B:
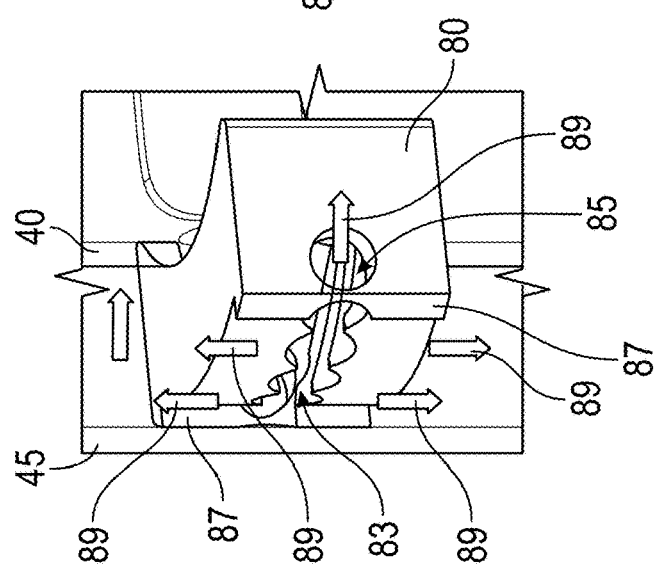
Figure 6A:
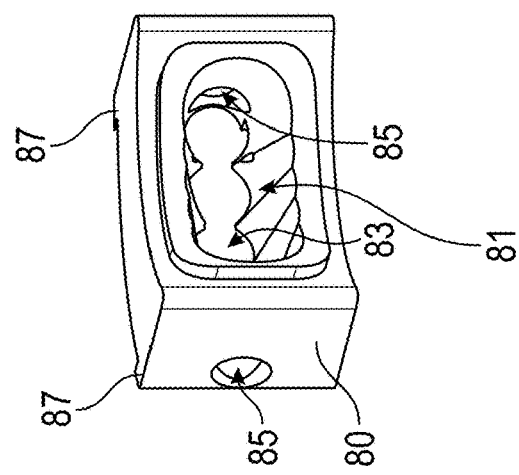

FIGS. 6A-6C depict views of an orifice body in the form of a lateral orifice according to one or more embodiments. FIGS. 6A-6C depict embodiments of a lateral orifice 80. FIG. 6A depicts a perspective view of lateral orifice 80 looking into an orifice inlet 81, such as of a fluid flowing into lateral orifice 80. FIG. 6B depicts a second perspective view of lateral orifice 80 looking into an outlet window 83, with lateral orifice 80 in place between a first chamber wall 40 and a second chamber wall 45. FIG. 6B also depicts a general flow direction 8. Finally, FIG. 6C depicts lateral orifice 80 proximate to an associated flow passage 41 of first chamber wall 40, such as if in an exploded view of the two parts that couple together.

Lateral orifice 80 also includes a pair of round orifice outlets 85 along with outlet window 83, which is opposite orifice inlet 81. The outlet window functions as a viewing window and another orifice outlet. Therefore, in FIGS. 6A-6C, outlet window 83 and two orifice outlets 85 serve as the flow restrictions.

Furthermore, when in position within the annulus between first chamber wall 40 and the second chamber wall, a pair of lateral orifice spacers 87 provide clearance between outlet window 83 and the second chamber wall to allow fluid flow. The fluid traversing lateral orifice 80 through outlet window 83 is shown by the downward and upward arrows 89 of FIG. 6B.

Due to the inclusion of lateral orifice 80, the fluid flow path through testing apparatus 500 (FIGS. 5A and 5B) may change as compared to the testing apparatus without a lateral orifice 80, such as testing apparatus 100 (FIG. 1). Specifically, for the embodiment shown in FIGS. 5A-5B and 6A-6C, first, fluid diverts from general flow direction 8 to enter lateral orifice 80 via orifice inlet 81. Fluid then exits lateral orifice 80 via two orifice outlets 85 and outlet window 83. Since orifice outlets 85 are not opposite orifice inlet 81, fluid exiting via orifice outlet 85 must again divert. Finally, because of the limited distance of lateral orifice spacers 87, fluid flowing out of outlet window 83 is shortly diverted either in or opposite general flow direction 8 within annulus 43. The small distance between the outlet window and the inner surface of second chamber wall (maintained here by the lateral orifice spacers) may add to the tortuous nature of the fluid path. Accordingly, as depicted using arrows 89 in FIG. 6B, the fluid flow path from the first chamber interior 42 into annulus 43 may be considered tortuous.

FIG. 6C depicts orifice inlet 81 adjacent to flow passage 41 but offset from its final, coupled position (such as in an exploded-type view). FIG. 6C further depicts an embodiment of orifice inlet 81 that includes a lip 82 having a shape that complements flow passage 41 in first chamber wall 40. Lip 82, when positioned relative to flow passage 41 while coupled with first chamber wall 40, may help maintain the position of orifice inlet 81 relative to flow passage 41 to facilitate a smooth fluid flow into orifice inlet 81. As well, lip 82 may be configured to prevent any fluid bypassing the flow restrictions (meaning two orifice outlets 85 and outlet window 83) when lateral orifice 80 is in position.

The configuration of the lateral orifice may be such that an egress path is present, such as a fluid flow path via one or both of orifice outlet and outlet window. In some embodiments, the fluid flow path may occur in one or multiple directions, such as upwards, downwards, and sideways as depicted by fluid flow path arrows 89 in FIG. 6B. In some embodiments, the fluid flow path may be in alignment with both the device central axis 6 and the general flow direction 8 after egressing from lateral orifice. For example, in FIG. 6B, there are fluid flow path arrows 89 moving downward in parallel with the device central axis 6 and aligned with general flow direction 8. In some other embodiments, the fluid flow path may not be in alignment with either the device central axis 6 or general flow direction 8 after egressing from lateral orifice. For example, in FIG. 6B, there are fluid flow path arrows 89 moving normal to the alignment of the device central axis 6 and to general flow direction 8. In yet some other embodiments, the fluid flow path may be in alignment with the device central axis 6 but is counter to the general flow direction 8 after egressing from lateral orifice. For example, in FIG. 6B, there are fluid flow path arrows 89 moving upwards—in alignment with the device central axis 6 but counter to general flow direction 8.

In embodiments of the testing apparatus, the fluid flow path may depend on the design of one or both of the lateral orifice and the orifice inlet. In one or more embodiments, fluid may exit the lateral orifice only via the fluid outlet(s) and not via the outlet window, for example, if the outlet window is closed with a transparent material or is abutting the second chamber wall without a flow outlet, a recess, or a lateral orifice spacer.

In one or more embodiments, the lateral orifice may be configured as a partial annular shape designed to conform with the flow passages and to seal against the first chamber wall to prevent fluid bypass of the flow restriction(s) defined by the lateral orifice.

Fluid flowing within the first chamber interior prior to entering the lateral orifice (meaning upstream from lateral orifice) may be flowing in a parallel manner to the device central axis and along the general flow direction of the testing chamber within the first chamber wall. In some embodiments, the axial direction of the first chamber wall may be vertical or approximately vertical; therefore, the fluid may be flowing substantially vertically—in a downward direction—due to gravity prior to encountering the lateral orifice. In one or more embodiments, the fluid direction into the opening of the orifice inlet (meaning the direction fluid flows into the orifice inlet) may not be parallel or substantially parallel with the device central axis or the first chamber wall. Fluid flowing from the first chamber into the lateral orifice via the orifice inlet may need to deviate from its prior flow direction along the general flow direction. Consequently, for example, a fluid traversing the lateral orifice may not flow parallel to or in alignment with the general flow direction at all times; rather, the fluid flow may deviate from the general flow direction. Placement of the lateral orifice outside the flow passage of the first chamber wall may divert the fluid flow from alignment with the device central axis, which may more closely simulate the geometry and flow dynamics experienced in a wellbore near a lost circulation zone. In some embodiments, the fluid flow into the orifice inlet may not be in alignment with either the device central axis or the general flow direction. In some embodiments, the fluid flow into to the opening of the orifice inlet may be substantially perpendicular to the device central axis.

As depicted in FIGS. 6A-6C, orifice inlet 81 and outlet window 83 of lateral orifice 80 are formed of conical perforations. Both orifice outlets 85 are round. One or more embodiments of the lateral orifice may include flow restriction(s) that serve to more closely replicate natural geologic formations, such as fissures, vugs, crevices, and fractures. For example, the configuration seen in FIGS. 4A and 4B may be implemented as a lateral orifice 80.

The lateral orifice may be machined via subtractive manufacturing or via additive manufacture techniques. Additive manufacturing may permit the lateral orifice to include more complex geometry such that the flow restriction(s) more closely simulates natural geologic formations. The configuration for this additive manufacture product may be based upon 3D scans of natural geologic formations or on 3D artists renderings of naturally inspired or artificial shapes.

In some embodiments, the lateral orifice may be partially or fully transparent. A transparent lateral orifice has many of the same observational benefits as previously described, especially for the observation of the interaction between LCM and the flow restriction(s) of the lateral orifice and, generally, the behavior of dual-phase flow traversing the lateral orifice.

In one or more embodiments, the exit flow path via one or both of orifice outlet and outlet window may be sufficiently large to not restrict the fluid flow. In such an embodiment, the fluid flow may be restricted by either the shape or size, or both, of the orifice inlet(s), such that the orifice inlet(s) serves as the flow restriction(s).

The thickness of the lateral orifice in the radial direction (meaning, perpendicular to the general flow direction), and thus the depth of the orifice inlet, may depend upon the size of the annulus. A thick lateral orifice located within the annulus may permit the orifice inlet to simulate a deep fissure. Such a geometry may allow for the testing of deformation processes like crushing and stretching of LCM, which in some instances and for some types of LCM (for example, resins or rubber composites or during the formation of resins) may occur in a crevice or vug.

In one or more embodiments, a testing chamber may include more than one orifice body. Such a testing chamber may include orifice plate(s) (such as orifice plate 63 in FIGS. 3A-3C), artificial formation plug(s) (such as artificial formation plug 65 in FIGS. 4A and 4B), lateral orifice(s) (such as lateral orifice 80 in FIGS. 5A, 5B, 6A-6C, 9, and 11), or combinations thereof.

In one or more embodiments, a testing chamber may include more than one form of flow restriction. The flow restrictions included in a testing chamber may include irregular flow restriction(s) defined by flow obstruction(s) (such as simulated rock pile 77 in FIG. 3C); flow passage(s) (such as flow passages 41 in FIGS. 8 and 10) defined by the first chamber wall; perforation(s) defined by orifice body(s); or combinations thereof. Flow restriction(s) in the form of perforation(s) may include hole(s) (such as hole 71 in FIGS. 1 and 3A), slot(s) (such as slot 73 in FIG. 3B), pore(s) (such as pore 79 in FIG. 4B), orifice inlet(s) (such as orifice inlet 81 in FIGS. 6A-6C, 9, and 11), outlet window(s) (such as outlet window 83 in FIGS. 6A-6C, 9, and 11), orifice outlet(s) (such as orifice outlet 85 in FIGS. 6A-6C), or combinations thereof. Such perforations may be defined by any type of orifice body, including orifice plate(s) (such as orifice plate 63 in FIGS. 3A-3C), artificial formation plug(s) (such as artificial formation plug 65 in FIGS. 4A and 4B), lateral orifice(s) (such as lateral orifice 80 in FIGS. 5A, 5B, 6A-6C, 9, and 11), or a combination.

In some embodiments, the testing chamber may be configured such that the flow restrictions vary from largest to smallest when moving from the fluid inlet conduit to the fluid outlet conduit. Employing multiple flow restriction forms, multiple orifice body configurations, or both, may help simulate downhole environments with both man-made and natural obstructions and voids. Such configurations may help predict not only proper LCM systems to use but also avoid the use of LCM systems that may interfere with downhole equipment and operations.

Downhole, deployed LCM in a plugged loss zone are frequently perturbed by movement proximate to their location, such as the traversal of a bottom hole assembly (BHA) or the rotation of a drill pipe. Such actions change the flow dynamics of fluid proximate to lost circulation zone, including changing the differential pressure keeping the deployed LCM in place.

In one or more embodiments, the testing apparatus may include an integrity wiper for the testing apparatus. In some embodiments, the integrity wiper may be in the form of a piston that may be rotated, reciprocated, or both, past lateral orifice(s) that have been plugged using LCM to simulate wellbore fluid disturbances, such as turbulent disruptions to flow, such as back and counter-flow.

FIGS. 7A and 7B depict an integrity wiper according to one or more embodiments. FIG. 7A depicts an enlarged view of a downstream end 23 of testing apparatus 700 having a testing chamber 20 that includes both a first chamber wall 40 and a second chamber wall 45, similar to the depiction in FIG. 5B. Again, chamber connector 48, downstream cap 49, and fluid outlet conduits 19 are shown. Furthermore, two flow passages 41 in first chamber wall 40 are each proximate to one of two lateral orifices 80.

FIG. 7A also shows integrity wiper 90, which includes an agitation component in the form of a head 91 coupled on a shaft 95. Head 91 is shown positioned within first chamber interior 42. Shaft 95 extends through downstream cap 49. FIG. 7B depicts an embodiment of an integrity wiper 90 outside of testing chamber 20. Integrity wiper 90 again includes an agitation component in the form of a head 91, which is mounted on a shaft 95. Head 91 has throughholes 93.

LCM is intended to obstruct fluid flow through flow restrictions. Movements of the agitation component(s) may produce fluid agitation within or proximate to the flow passage(s), which may directly serve as the flow restriction(s) themselves or may be located proximate to the flow restriction(s). The integrity wiper may be used to study the impact of fluid agitation on a partially or fully clogged flow restriction. Consequently, the integrity wiper may simulate the agitation encountered by a partially or fully remediated pore or vug in a real-world device caused by the movement of downhole components, for example, by a bottomhole assembly (BHA) or a rotating drill pipe.

In some embodiments, the integrity wiper may include one or more agitation components. The agitation component(s) may be configured to generate or increase fluid motion (for example, flow disruption, agitation, or both) within or near the flow passage(s). The agitation component(s) may or may not have a larger radial diameter than the shaft so as to extend from the shaft radially. An agitation component may or may not be located at a terminus of the integrity wiper within the first chamber interior. In the embodiment depicted in FIGS. 7A and 7B, head 91 serves as the agitation component of integrity wiper 90. Head 91 has a larger radial diameter than shaft 95 and is located at a terminus of integrity wiper 90 within first chamber interior 42.

In some embodiments, the agitation component(s) may be configured in the shape of a downhole tool, such as a BHA or a drill pipe, or other equipment used in the downhole environment. In some embodiments, the integrity wiper may be designed to simulate the external diameter profile of a drill string. One or more embodiment of such an integrity wiper may have an external diameter profile that varies along the device central axis direction between the shaft and the agitation component(s). Such a wiper may be configured to simulate different scenarios, such as a drill string that has larger-diameter connectors along its length.

In one or more embodiments, the agitation component(s) may correspond in shape with the interior shape of the first chamber wall. In one or more embodiments, the agitation component(s) may have an outer radial diameter that is approximately the same as the interior radial diameter of the first chamber wall so as to create a frictional seal with the interior shape of the first chamber wall. In such a configuration, the agitation component(s) may serve to produce fluid motion (for example, flow disruption, agitation, or both) near a partially or fully clogged flow restriction and to physically manipulate any LCM extending beyond the flow restriction into the first chamber interior. In one or more embodiments, the agitation component(s) may correspond more loosely to the shape of first chamber wall. In such a configuration, the agitation component(s) may largely serve to introduce fluid agitation on a partially or fully clogged flow restriction.

In some embodiments, the shaft of the integrity wiper may extend through the downstream cap, the upstream cap, or both. Thus, in some embodiments, the downstream cap, the upstream cap, or both may define a hole through which the shaft extends. For example, in FIG. 7A, shaft 95 extends through downstream cap 49.

In some embodiments, the downstream cap, the upstream cap, or both, may frictionally couple to the shaft to create both a fluid seal and permit movement of the integrity wiper within the first chamber interior using the shaft. To that end, in some embodiments, the hole defined by the downstream cap, the upstream cap, or both, through which the shaft extends may be coated with or formed of a low friction material, a flexible material, or both (for example, a polymer gasket). The fluid seal, the ease of movement, or both, may be improved by employing such a material at the interface between the shaft and the downstream cap, the upstream cap, or both.

The shaft may be used to move the agitation component(s) within the first chamber interior, for example rotationally around the device central axis, axially along the device central axis, or both. The movements of the agitation component(s) may be asymmetrical (meaning, in a single direction), reciprocating (meaning, alternatingly in two opposing directions), or both (for example, asymmetrical rotation and reciprocating axial motion). Movement of the shaft may be manual or automated.

One or more embodiments may include one or more throughholes in the agitation component. As depicted in FIG. 7B, head 91 has four rounded throughholes 93. These through holes allow the integrity wiper to be driven past the flow passages without blocking the fluid flow, significantly pushing the fluid, or creating a hydraulic lock. Thus, the fluid as well as any extra LCM (that is, LCM that is not incorporated into the plugged zone of an orifice body) may pass through the holes when the integrity wiper is being manipulated.

The geometry and number of through holes in the head may vary. In one or more embodiments, through holes may be round, oval, square, curved slot, rectangular, other common geometrical shapes, or a combination of these. In one or more embodiments, and not dissimilar to the configuration shown in FIG. 7B, the head may resemble a spoked wheel such that the through holes have a truncated pie-shape.

In some embodiments, the shaft may have any sufficient length. The shaft may have a sufficient length such that one or more agitation component (for example, the head) of the integrity wiper, when moved laterally along the device central axis, can be positioned either upstream or downstream of the flow passage. The shaft may have a sufficient length such that, when an agitation component (for example, the head) is laterally positioned both upstream and downstream of the flow passage, a portion of the shaft extending from the first chamber interior is sufficient for manipulation.

The shaft may have a sufficient length such that one or more agitation component (for example, the head) of the integrity wiper, when moved laterally along the device central axis, can be positioned proximate to either the downstream cap or the upstream cap. The shaft may have a sufficient length such that, when an agitation component (for example, the head) is laterally positioned proximate to both the upstream cap and the downstream cap, the portion of the shaft extending from the first chamber interior is sufficient for manipulation.

Methods other than manipulation of a shaft may be used to rotate, reciprocate, or both, the integrity wiper (including the agitation component(s)) within the first chamber interior. For example, a portion of the integrity wiper may be magnetic. A non-contacting magnet located external to the second chamber wall may be used to maneuver the integrity wiper within the first chamber interior. Movement of such a non-contacting magnet may be manual or automated.

One or more embodiments of the testing apparatus may accommodate interchangeable integrity wipers. In such a system, a first integrity wiper may be removed from the testing apparatus and a second integrity wiper may be introduced into the testing apparatus. Interchangeable integrity wipers may facilitate the study of the impact of multiple simulated downhole tools.

One or more embodiments of the testing apparatus may accommodate integrity wipers with interchangeable agitation components (for example, heads). In such a system, an integrity wiper may be removed from the testing apparatus, the head of the entire integrity wiper may be replaced, and the integrity wiper may be introduced into the testing apparatus. Interchangeable integrity wiper heads may similarly facilitate the study of the impact of multiple simulated downhole tools.

The integrity wiper may be fabricated from any material, such as a polymer, a metal (such as stainless steel), or a combination of materials. The respective components of integrity wiper, such as the head and the shaft, may be fabricated from dissimilar materials. In some embodiments, the head may be partially or fully formed of or coated with a soft material or a low friction material. The use of such a low friction or soft material in the head may help protect the interior of first chamber wall from physical damage, such as scraping or scuffing, due to the movement of the head. As discussed earlier, the head may be formed partially or fully of a magnetic material.

Figure 8:
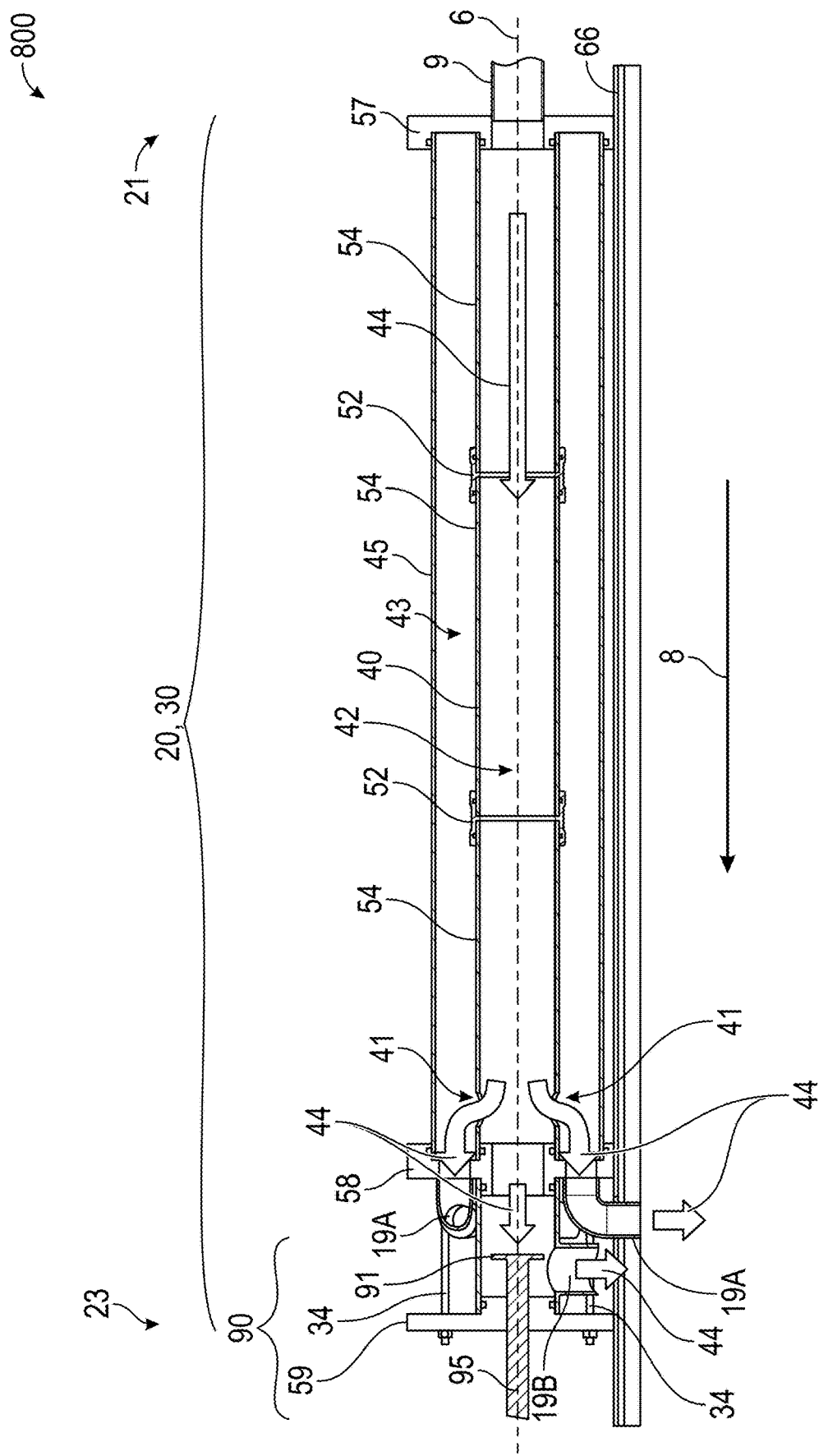
FIG. 8 depicts an LCM testing apparatus with a first and second chamber wall according to one or more embodiments.

FIG. 8 depicts an embodiment of a large- or full-scale LCM testing apparatus with a first and second chamber wall according to one or more embodiments. FIG. 8 shows device central axis 6 (dashed centralized line) and general fluid flow direction 8 (arrow).

Apart from the scale, testing apparatus 800 differs at least from previously-described embodiments in that 1) testing apparatus 800 includes multiple fluid outlet conduits such that not all fluid and LCM flows egress from the same fluid output flow channel; 2) the first chamber wall is formed from multiple pipe-shaped components that may be engaged and disengaged from one another; 3) the first and second chamber walls extend upstream and are coupled to the upstream cap; 4) since testing apparatus 800 lacks an LCM inlet, both the LCM and the fluid are both introduced into the chamber body via the fluid inlet conduit; and 5) testing apparatus 800 is substantially-horizontal or horizontally oriented, which does not exploit gravity as the main drive for fluid flow through the testing apparatus. The last aspect is important as many lost circulation zones appear in lengthy portions of wellbores configured in a deviated, substantially horizontal, or horizontal fashion.

FIG. 8 shows testing apparatus 800 having a testing chamber 20 (with an upstream end 21 and a downstream end 23), fluid inlet conduit 9, and two first fluid outlet conduits 19A and a second fluid outlet conduit 19B. Testing chamber 20 includes chamber body 30, which includes a first chamber wall 40, a second chamber wall 45, an upstream cap 57, a downstream cap 59, and a chamber connector 58. Chamber connector 58 may be secured to downstream cap 59 using tie bars 34 in some embodiments.

Testing chamber 20 is shown resting on a horizontal base plate 66; however, testing apparatus 800 may incorporate a resting surface, such as horizontal base plate 66, that is inclined, declined, vertical, substantially vertical, deviated, substantially horizontal, or horizontal. As well, in some embodiments there may not be a base plate; the testing chamber may rest directly on a surface, such as a concrete floor, a skiff, a truck bed, a gravel pad, or bare earth.

First chamber wall 40 and second chamber wall 45 are capped near an upstream end 21 of testing chamber 20 by upstream cap 57. First chamber wall 40 is coupled to downstream cap 59 near a downstream end 23 of testing chamber 20. A portion of first chamber wall 40 couples to and extends through chamber connector 58 and another second portion of first chamber wall 40 extends within the interior of second chamber wall 45, as previously described. However, in contrast with testing apparatus 500 (FIGS. 5A and 5B), the portion of first chamber wall 40 that is not arranged concentrically within second chamber wall 45 is on a downstream side of chamber connector 58 instead of on an upstream side of chamber connector 48 (see FIGS. 5A and 5B).

In some embodiments, any component downstream from the fluid conduit inlet, including the chamber connector, the downstream cap, the first chamber wall, or the second chamber wall, may be coupled to a fluid outlet conduit. In FIG. 8, two first fluid outlet conduits 19A couple to chamber connector 58 and second fluid outlet conduit 19B couples to first chamber wall 40, between downstream cap 59 and chamber connector 58.

In one or more embodiments, the annulus, the first chamber interior, or both, may be in fluid communication with one or more fluid outlet conduits. In FIG. 8, first chamber interior 42 is in fluid communication with second fluid outlet conduit 19B, and annulus 43 is in fluid communication with first fluid outlet conduit 19A.

FIG. 8 shows two flow passages 41 defined by first chamber wall 40 that are positioned towards downstream end 23 of first chamber wall 40 and proximate to and upstream of chamber connector 58. A fluid flow path is shown via arrows 44. In such an embodiment, within the chamber body the first chamber interior is in fluid communication with the annulus through the one or more flow passage in first chamber wall, similar to the previously-described embodiments.

In some embodiments of a testing apparatus having a first and second chamber wall, the flow passage(s) may be configured to serve as the flow restriction(s). The flow passages are defined by the first chamber wall; therefore, the flow restriction(s) are also defined by the first chamber wall. Such an embodiment may be used to test mitigating techniques for lost circulation zones caused by damage to a casing wall or a large, simple opening in the wellbore wall.

Some embodiments of the testing apparatus may be configured such that they may operate either without orifice body(s) or with interchangeable orifice body(s). In some embodiments, the testing apparatus may thus be fitted with one or more interchangeable lateral orifices, such as lateral orifice 80 (FIGS. 5A and 5B), where each lateral orifice may be positioned proximate to a flow passage to further restrict the fluid flow between the first chamber interior and the annulus. In such an embodiment, the flow restriction(s) may be defined by the orifice body(s) instead of by the first chamber wall. As previously described in prior embodiments, the fluid flow pathway through such flow restrictions may deviate from being parallel or aligned with the device central axis. As well, the fluid flow pathway through such flow restrictions may deviate from being parallel or aligned with the general fluid flow direction.

In some embodiments, the testing chamber may also include an integrity wiper, which has an agitation component coupled to a shaft, as previously described. In FIG. 8, head 91 is shown positioned within first chamber interior 42 while shaft 95 extends through downstream cap 59 and outside of first chamber interior 42.

In some embodiments, the integrity wiper may take the form of a downhole component or of a model of a downhole component. In FIG. 8, integrity wiper 90 is shown having the form of a mounting flange, which is a common downhole component that may be encountered in a real-world lost circulation zone.

Some embodiments of the testing apparatus may represent a full-scale horizontal testing chamber fabricated from downhole components, such as tool joints and casing configured for use in a wellbore. For example, first chamber wall 40 in FIG. 8 is configured of three lengths of casing 54 coupled in series with tool joints 52. Flow passages 41 are defined by the downstream-most length of casing 54. The tool joints may affect the flow of the fluid.

As a practical example, consider the configuration of a coaxial casing system such as described previously. The first chamber wall and the second chamber wall are largely modular assemblies of commercial products. The first chamber wall may be comprised of a commercially-available casing with a 9.625 inch outer diameter, a 8.5 inch inner diameter, and a weigh of 53.5 pounds per foot. Similarly, the second chamber wall may be formed of a single 20 inch outer diameter casing that weighs 94 pounds per foot. One having ordinary skill in the art will appreciate how the length and (absolute and relative) diameter of the first chamber wall and the second chamber wall may be varied by adapting commercially-available components. By employing identical or substantially similar downhole components, experimental results generated using such a testing chamber may more accurately model the performance of LCM in a downhole environment.

Figure 9:
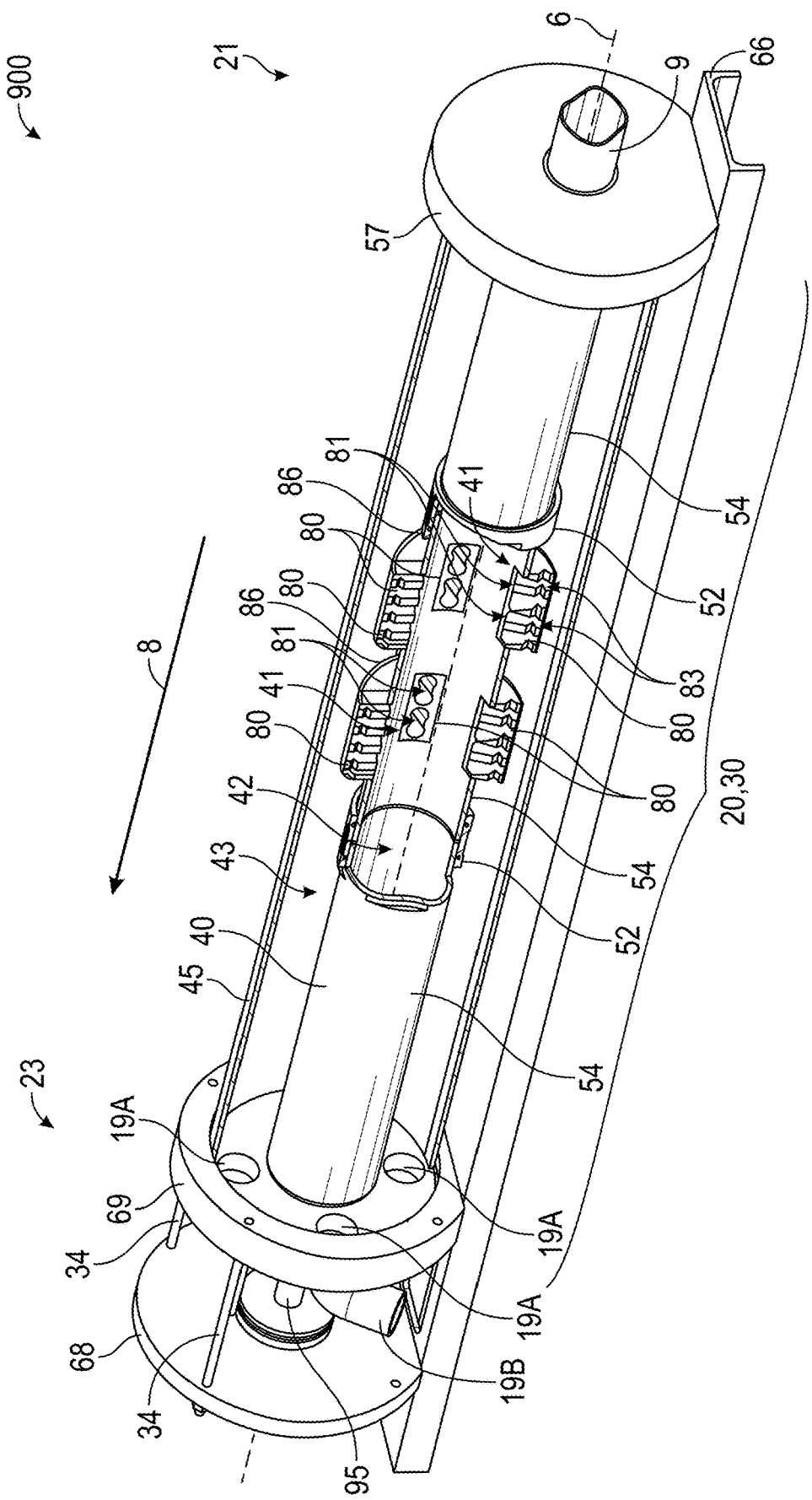
FIG. 9 depicts an LCM testing apparatus with a first and second chamber wall according to one or more embodiments.

FIG. 9 depicts an additional embodiment of a testing apparatus 900 that is similar to testing apparatus 800 (FIG. 8). FIG. 9 depicts a partial reveal perspective view of testing apparatus 900. The differences between testing apparatus 900 and other previously-described embodiments are at least: 1) the first and second chamber walls may extend equal distances and be arranged concentrically along their entire lengths, 2) all fluid outlets are disposed through the downstream cap, and 3) the use of at least one lateral orifice that may be different than previously described.

In some embodiments of the testing chamber, a first chamber wall and a second chamber wall may be of equal lengths and may be arranged concentrically along their entire lengths. In such embodiments, the testing chamber may not include a chamber connector. In such embodiments, a first chamber wall and a second chamber wall may couple near an upstream end of the testing chamber with an upstream cap. In such embodiments, the first chamber wall and the second chamber wall may couple near a downstream end of the testing chamber with a downstream cap. For example, in contrast with previously described testing apparatuses 100, 500, 800 (FIGS. 1, 5A, 5B, and 8), testing apparatus 900 lacks a chamber connector 48, 58 (FIGS. 5A, 5B, and 8).

FIG. 9 depicts (through partial reveal perspective view) several lateral orifices 80 arranged around the external surface of a middle casing 54 of first chamber wall 40, where each lateral orifice 80 is associated with a flow passage 41 defined by middle casing 54. Lateral orifices 80 are coupled to the exterior of middle casing 54 with one or more collars 86. In this instance, each lateral orifice has two orifice inlets and two outlet windows, and each orifice inlet is positioned located opposite an outlet window. The position of each lateral orifice 80 is such that each flow passage 41 is fluidly aligned to a plurality of orifice inlets, for example, two orifice inlets 81, of testing apparatus 900. The orifice inlets are configured to serve as the flow restrictions.

In using an embodiment of testing apparatus, such as testing apparatus 900, one or more lateral orifices may be interchangeable between tests, such as to change the configuration of the fluid flow path from a first chamber interior, through a flow passage, and into the annulus. Some embodiments may include one or more collars or a similar-acting structure to couple one or more lateral orifices onto the exterior of the first chamber wall, such that the lateral orifice is associated with a flow passage. The collar may facilitate reconfiguration of or removal of the lateral orifice between tests. Using a collar to couple a lateral orifice in place may limit the need to permanently couple or connect the lateral orifice to the surface of the first chamber wall, the second chamber wall, or both.

In an embodiment having a collar, the radial distance between the first chamber wall and second chamber wall may need to be equal to or greater than the radial thickness of the lateral orifice and the collar. Additionally, the collar may allow the radial distance between the first chamber wall and second chamber wall to be greater (for example, substantially greater) than the radial thickness of the lateral orifice. Such an embodiment of the testing apparatus may accommodate interchangeable lateral orifices with a wider range of radial thicknesses since the lateral orifice is not held in place by the precise radial fit between the first and second chamber bodies. Additionally, a collar may facilitate the incorporation of components with larger manufacturing tolerances. Finally, a distance between the collar or lateral orifice and the second chamber wall may simplify assembly, reconfiguration, or both, of the testing chamber.

Also included in FIG. 9 is a shaft support plate 68. Shaft support plate 68 defines a hole through which a shaft 95 of an integrity wiper extends. Shaft support plate 68 supports shaft 95 and proper aligns shaft 95 along a device central axis 6.

Figure 10:
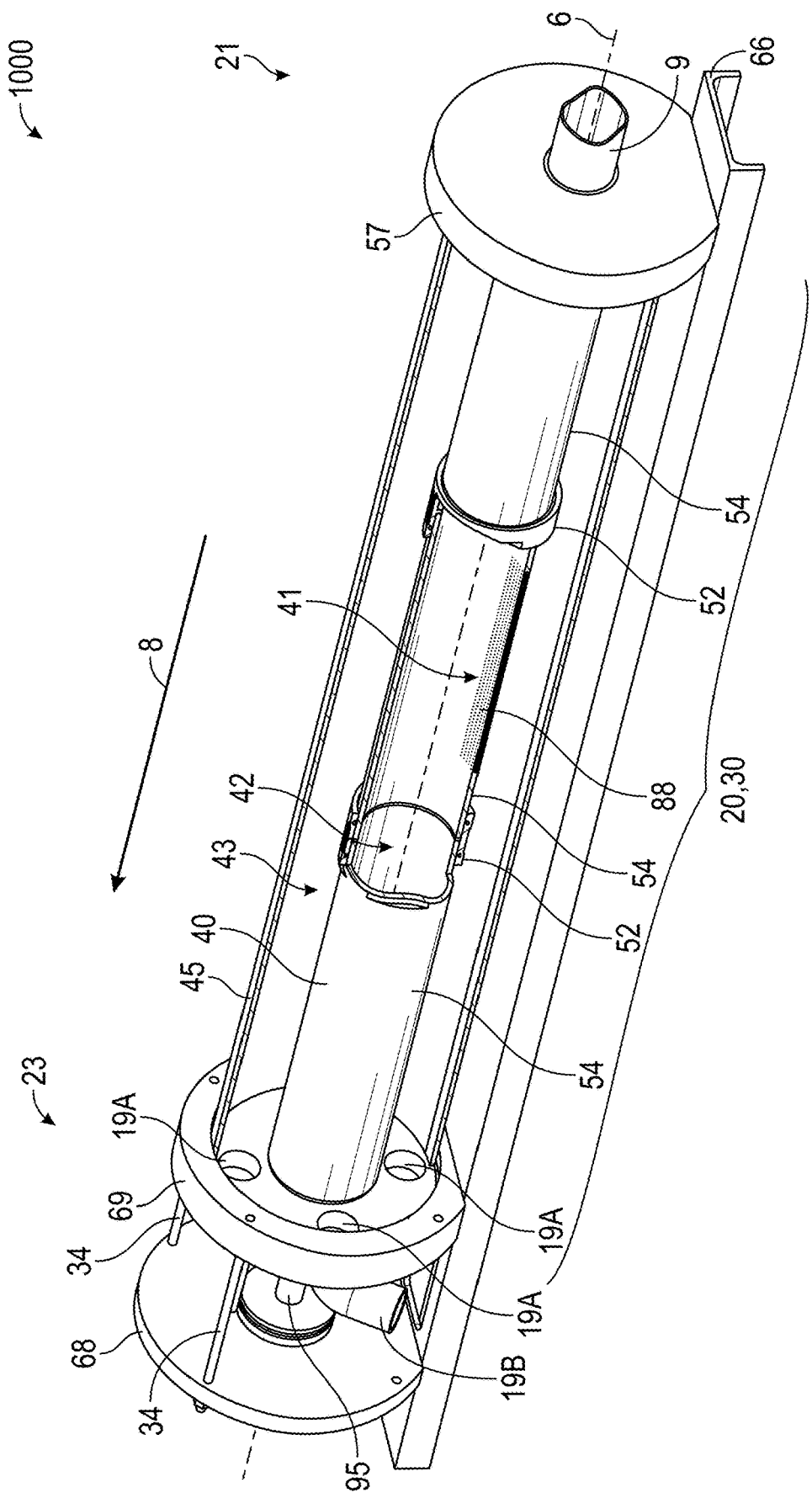
FIG. 10 depicts an LCM testing apparatus with a first and second chamber wall according to one or more embodiments.

FIG. 10 depicts an additional embodiment of a testing apparatus 1000 that is similar to testing apparatus 900 (FIG. 9). FIG. 10 depicts a partial reveal perspective view of testing apparatus 1000. The difference between testing apparatus 1000 and other previously-described embodiments are at least how, instead of employing lateral orifices or other orifice bodies, a plurality of flow passages serve as flow restrictions.

In FIG. 10, the flow path between first chamber interior 42 and annulus 43 is through a plurality of flow passages 41 defined by first chamber wall 40. The plurality of flow passages 41 may simulate a region of porosity 88. In some instances, such as testing apparatuses 800 and 1000 as depicted in FIGS. 8 and 10, a flow passage or a set of flow passages may serve as the fluid constriction point between first chamber interior and annulus. In such an instance, the flow passage or set of flow passages may be configured to serve as one or more flow restrictions, restricting the traversal of the fluid and the LCM flowing along the fluid flow path.

Reconfiguring between embodiments of the testing device may only require the exchange of a differently configured middle casing. As described previously, the first chamber wall may be formed of multiple casings that are removably coupled by tool joints. Consequently, one having skill in the art will appreciate how casings having different configurations may be easily managed and changed between tests. For example, in comparing testing apparatus 900 (FIG. 9) with testing apparatus 1000 (FIG. 10), only middle casing 54 of first chamber wall 40 (along with lateral orifices 80 attached with collars 86 to first chamber wall 40 of testing apparatus 900) is different. All other components of both testing apparatuses 900 and 1000 are identical.

Some embodiments of such an interchangeable casing may include a flow passage or a set of flow passages configured to serve as the flow restriction(s), having any number, size(s), shape(s), and arrangement(s) of flow passage(s). For example, middle casing 54 of testing apparatus 1000 includes a plurality of flow passages 41 in a region of porosity 88 that serve as flow restrictions. Further, some embodiments of such an interchangeable casing may include one or more flow passage configured to accommodate one or more interchangeable lateral orifice. For example, middle casing 54 of testing apparatus 900 (FIG. 9) includes larger flow passages 41 that accommodate lateral orifices 80. Finally, some embodiments of such an interchangeable casing may include one or more permanently attached lateral orifices, which are located proximate to and fluidly connected with the flow passage(s).

Figure 11:
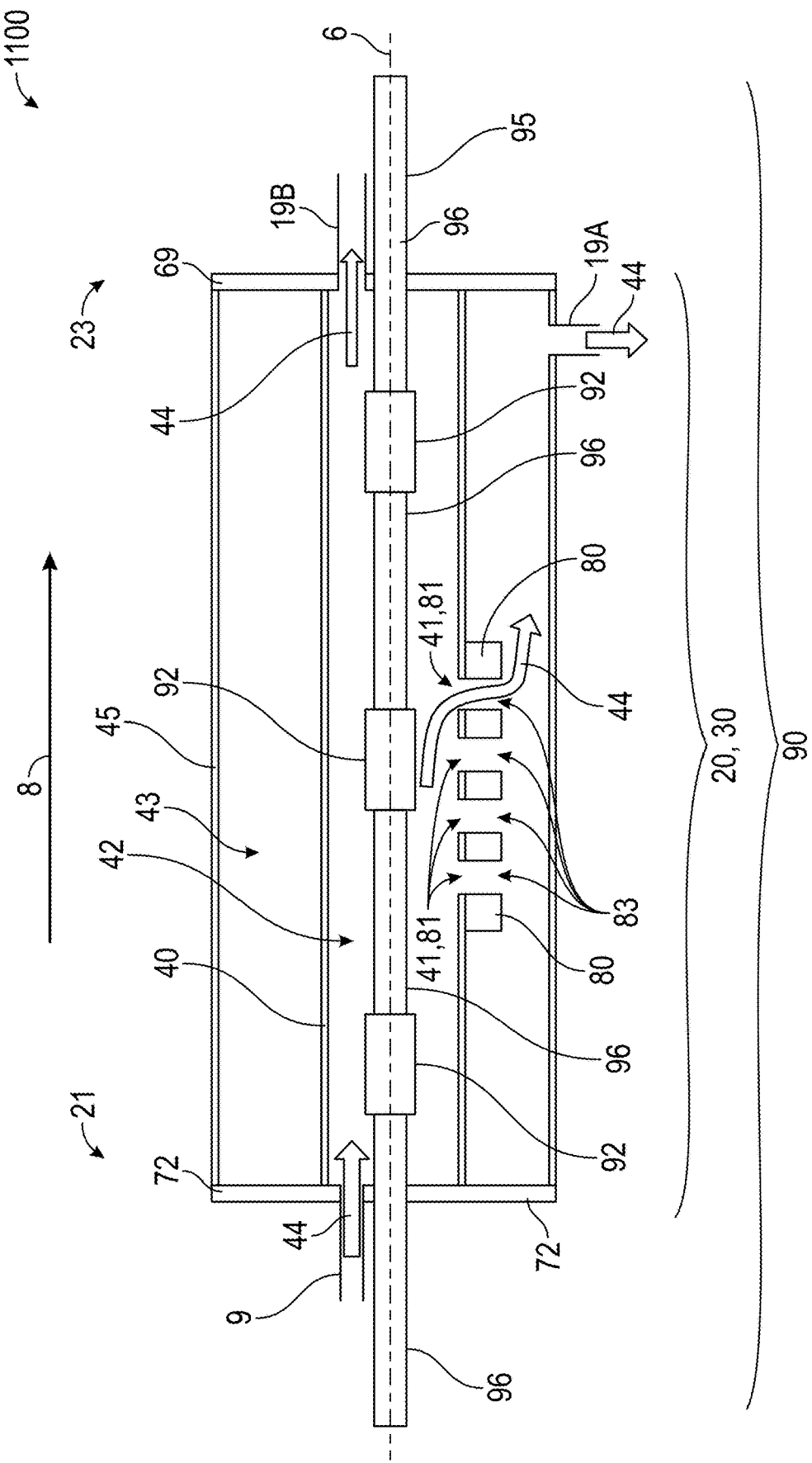
FIG. 11 depicts an LCM testing apparatus with a first and second chamber wall according to one or more embodiments.

FIG. 11 depicts a cross section of an embodiment of a testing apparatus 1100, where the integrity wiper is configured to simulate a drill string. Apart from the integrity wiper and the interaction between the integrity wiper and the upstream cap, the testing apparatus is similar to testing apparatus 900 of FIG. 9.

Integrity wiper 90 is configured to simulate the impacts of continued drilling on a lost circulation zone. In contrast with other embodiments of the testing apparatus, such as the testing apparatus 700, the integrity wiper 90 extends the entire length of first chamber interior 42 and passes through both upstream cap 72 and downstream cap 69. Further, as shown in the embodiment in FIG. 11, integrity wiper 90 may be formed of drill pipe sections 96 coupled by pipe connectors 92.

In FIG. 11, integrity wiper 90 is shown with four drill pipe sections 96 coupled by three pipe connectors 92; however, any number of drill pipe sections and pipe connectors may be used.

Each pipe connector of the integrity wiper may or may not be roughly equivalent in size. Further, each pipe connector of the integrity wiper may or may not be the same pipe connecting components. Each drill pipe section of integrity wiper may or may not be roughly equivalent in size.

In some embodiments of the testing apparatus, the shaft extends the entire length of the first chamber interior. Consequently, as discussed previously, in some embodiments, the shaft of the integrity wiper may extend through both the downstream cap and the upstream cap. Further, in some embodiments, the shaft of an integrity wiper may be formed of multiple drill pipe sections. Therefore, one of the upstream drill pipe sections (for example, the furthest upstream drill pipe section) passes through the upstream cap and one of the downstream drill pipe sections (for example, the furthest downstream drill pipe section) passes through the downstream cap. In such embodiments, as discussed previously, the downstream cap and the upstream cap may each frictionally couple to one of the drill pipe sections to create both a fluid seal and to permit movement of the integrity wiper within the first chamber interior using one or both ends of the shaft. In FIG. 11, shaft 95 is formed of three drill pipe sections 96. The furthest upstream drill pipe section 96 passes through and frictionally couples to upstream cap 72. Similarly, the furthest downstream drill pipe section 96 passes through and frictionally couples to downstream cap 69.

As discussed previously, in some embodiments the integrity wiper may include agitation component(s) configured to generate or increase fluid motion (for example, flow disruption, agitation, or both) within or near the flow passage(s). These agitation component(s) may have a larger radial diameter than the shaft such that they extend radially from the shaft. In the embodiment depicted in FIG. 11, the three pipe connectors 92 extend radially between the four downstream drill pipe sections 96. The pipe connectors 92 serve as agitation components of integrity wiper 90.

The portion of the drill pipe section that extends out of the downstream cap, out of the upstream cap, or both, may serve as a shaft for the integrity wiper. As previously described, the shaft may be used to radially rotate, axially reciprocate, or both, agitation component(s) within the first chamber interior along the device central axis. Such movements of the agitation component(s), in this case comprising one or more pipe connectors and drill pipe sections, may produce fluid motion (for example, flow disruption, agitation, or both) near the flow restrictions. LCM is intended to obstruct fluid flow at the flow restrictions, such as those simulated by lateral orifices or flow passages. The integrity wiper may be used to study the impact of fluid agitation on a partially or fully clogged flow restriction. The integrity wiper, through such motions, may simulate the agitation encountered by a partially or fully remediated pore or vug due to the movement of a downhole device, such as a BHA or a rotating drill pipe.

Each pipe connector may have any shape or size configured to move within the first chamber wall. The pipe connectors may correspond in shape with the interior shape of first chamber wall. The difference between the radial diameter of the pipe connectors and the interior diameter of first chamber wall may correspond with the real-world distance between the pipe connectors and a casing in a wellbore. Similarly, the difference between the radial diameter of the drill pipe sections and the interior diameter of the first chamber wall may correspond with the real-world distance between the drill pipe and the casing in a wellbore. The diameter difference between the pipe connectors and the drill pipe sections may reflect the real-world measurements of such components. To that end, the diameter difference between the pipe connector and the drill pipe section may be minimal, meaning the drill pipe section may have a diameter between about 0.01% and about 10% greater than pipe connector.

Some or all the components described previously and depicted in FIGS. 1-11 may be incorporated into embodiments of the testing apparatus. Other components not explicitly disclosed here may also be included in the testing apparatus. In view of the previous discussion and of FIGS. 1-11, one having skill in the art will appreciate the many combinations of components that may be incorporated into one or more embodiments of the testing apparatus according to this disclosure. Such embodiments of the testing apparatus may be incorporated into an LCM testing system.

FIG. 12 depicts an LCM testing system according to one or more embodiments. Testing system 1200 includes a testing apparatus 101 that is one component within a fluidly coupled circuit. This circuit serves to supply fluid to a testing chamber 20 of testing apparatus 101. A fluid inlet conduit 9 proximate to the upstream end 21 of testing chamber 20 is coupled to an upstream cap 37. A fluid outlet conduit 19 proximate to a downstream end 23 of testing chamber 20 is coupled to a downstream cap 39. Between upstream cap 37 and downstream cap 39 is a chamber body 30, which is defined by a chamber wall 31. Orifice body 60 is located within chamber body 30 and defines a hole 71 that serves as a flow restriction configured to restrict the traversal of the fluid and the LCM along the fluid flow path (partially indicated by arrow 33). FIG. 12 also shows a device central axis 6 (dashed centralized line) and a general fluid flow direction 8 (arrow).

Upstream of the fluid inlet conduit may be two sources of fluid: a test fluid reservoir and a fluid feed conduit. As shown in FIG. 12, a test fluid reservoir 1 may store and deliver fluid, such as previously described, either mixed with LCM or without LCM. Additionally, fluid may come from an outside source, such as a hose, through a fluid feed conduit 3. Directing at least one of these two fluids into testing apparatus 101, as shown in FIG. 12, may occur via a first flow direction valve 5. Also, a first flow control valve 7 to control the flow of fluids into testing apparatus 101 may be positioned between the first flow direction valve 5 and fluid inlet conduit 9. Although not shown, a pump may be used to convey the fluid into the testing apparatus. The two fluids may be supplied in any combination, including simultaneously or separately.

In one or more embodiments, a first flow control valve may include an analog or digital flow meter configured to control the individual flows from the test fluid reservoir and the fluid feed conduit. In one or more embodiments, the first flow control valve may be positioned to permit either the selection of a single fluid or the mixing of the fluids from test fluid reservoir and fluid feed conduit at a given ratio or formulation.

Testing system 1200, as shown in FIG. 12, is oriented in a vertical or substantially vertical manner. In one or more embodiments, testing reservoir 1 may be configured or positioned such that it is elevated or relatively higher than the testing apparatus to create a gravity-based pressure head. This may be the case even when testing apparatus is in a diverted, substantially horizontal, or horizontal configuration. The test fluid reservoir may be fitted with any combination of appropriate fixtures and access ports to support testing, such as filling and draining ports, air pressure and vapor displacement ports, safety pressure relief valves, and an internal LCM mix paddle (not depicted).

In one or more embodiments, the test fluid reservoir may be a closed vessel appropriately sized to contain the fluid mixed with lost circulation material. In one or more embodiments, the testing chamber and the testing system are configured for a operating pressure in a range of from about 0 to about 2,500 pounds per square inch (psi), such as about 0 to about 2,000 psi, such as about 0 to about 1,500 psi, such as about 0 to about 1,000 psi, such as about 0 to about 750 psi, such as about 0 to about 500 psi, such as about 0 to about psi, such as about 0 to about 300 psi, such as about 0 to about 200 psi, such as about 0 to about 100 psi, such as about 0 to about 75 psi, such as about 0 to about 50 psi, such as about 0 to about 25 psi, such as about 0 to about 20 psi, such as about 0 to about 14.7 psi (atmospheric pressure), such as about 0 to about 10 psi, such as about 0 to about 5 psi, and such as about 0 to about 1 psi. The vessel may be closed such that air backpressure may be applied, if required, to vary the test pressure within the testing apparatus and testing system. Thus, test fluid reservoir may be pressurized, in some instances, with pressure control component(s) such as an accumulator type system (not depicted). An accumulator type pressurization system may provide a maximum test pressure of approximately 2,500 pounds per square inch (psi) (~17.2 megapascals (MPa)). Alternatively, at least one air pressure port or one filling port on the test fluid reservoir may be left open to the environment such that a test may be conducted under atmospheric or surface pressure conditions (about 14.7 psi).

In some embodiments, some or all components of the testing system may be configured to operate at controlled temperatures, for example, greater than, at, or less than room temperature (about 20° Celsius). As discussed previously with respect to the testing apparatus, the intended operating temperatures of the testing system may influence the material selections for each component.

Some embodiments of the testing system may include temperature control component(s) to control (increasing, decreasing, or both) the temperature of the fluid prior to introduction into the testing apparatus via the fluid inlet conduit. In some embodiments of the testing system, one or more direct or indirect heating or cooling system (not depicted), for example, an electric heating system, a refrigeration system, or a fluid circulation system that circulates a heated or a cooled fluid may be included. Such temperature control components of the testing system may be located proximate to the test fluid reservoir, the fluid feed conduit, or both, or any other appropriate location upstream from the fluid inlet conduit.

Some embodiments of the testing system may include temperature control component(s) to control (increasing, decreasing, or both) the temperature of some or all components of the testing apparatus. In some embodiments of the testing apparatus, one or more direct or indirect heating or cooling system (not depicted), for example, an electric heating system, a refrigeration system, or a fluid circulation system that circulates a heated or a cooled fluid, may be included. In some embodiments, these component(s) may be located proximate to the chamber body to control the temperature of the fluid and LCM within the chamber interior.

In some embodiments, the testing system may include a second flow control valve and a second flow direction valve downstream of the fluid outlet conduit. The second flow direction valve may allow the fluid to be selectively directed to either a fluid exit conduit or a test fluid collector. In FIG. 12, the testing system is shown as configured such that a second flow control valve 17 and a second flow direction valve 15 are present downstream of fluid outlet conduit 19. Second flow direction valve 15 is selectively, fluidly coupled to both a fluid exit conduit 13 and a test fluid collector 11.

Finally, in some embodiments, a test fluid return conduit may fluidly couple the test fluid collector to the test fluid reservoir in order to recycle the fluid once it has passed through the testing chamber. This recycling may occur after the completion of a test in preparation for future tests or during a test to replenish the test fluid reservoir for continuation of the test. In FIG. 12, test fluid return conduit 10 fluidly couples test fluid collector 11 to test fluid reservoir 1 for reuse.

In one or more embodiments, the test fluid collector may be either an open vessel or a closed vessel. The test fluid collector may be fitted with an inlet port and an outlet/drain port (not depicted).

In one or more embodiments, the volume of the testing fluid reservoir and the testing fluid collector are associated with the flow rate capacity of the testing chamber. The minimum volume of the test fluid reservoir may be sufficiently large to ensure that, for example, the test chamber is continuously full during the period in which the test is conducted at a maximum fluid flow rate. In some embodiments, the test fluid collector may need to be at least as large as the test fluid reservoir such that the entire contents of the test fluid reservoir may be contained in the fluid collector by the end of the test. One of ordinary skill in the art may appreciate that no particular maximum volume of the test fluid reservoir or the test fluid collector may be defined because each may depend upon overall size constraints of the testing apparatus or the test chamber, and varying factors outside of the configuration of the testing apparatus, such as the maximum flow rate and test duration.

A person having skill in the art will appreciate the test fluid return conduit may include a pump for overcoming gravity if the test fluid reservoir is located at an elevation above the test fluid collector. Furthermore, the fluid entering the testing chamber via the fluid inlet conduit may be pressurized to further simulate pressures experienced downhole. This pressurization may occur via a pump or other means positioned anywhere upstream of testing chamber. Examples include within the test fluid reservoir, immediately after exiting the test fluid reservoir, upon entering the fluid feed conduit, immediately before the fluid inlet conduit, or along any of the connective piping upstream of the testing chamber.

In the embodiment provided for in FIG. 12, fluid inlet conduit 9 and fluid outlet conduit 19 are drawn as distinct, short fluid conduits; however, such limitations are not required. In one or more embodiments, one or both of the fluid inlet conduit and the fluid outlet conduit may be simple opening(s) at the axial end(s) of the testing chamber that are fluidly coupled to additional components upstream and downstream, respectively.

In one or more embodiments, the testing chamber and the testing system are configured for an operating volumetric fluid flow rate in a range of from about 0 to about 4,000 liters per minute (L/min), such as about 0 to about 3,500 L/min, such as about 0 to about 3,000 L/min, such as about 0 to about 2,500 L/min, such as about 0 to about 2,000 L/min, such as about 0 to about 1,500 L/min, such as about 0 to about 1,000 L/min, such as about 0 to about 750 L/min, such as about 0 to about 500 L/min, such as about 0 to about 400 L/min, such as about 0 to about 300 L/min, such as about 0 to about 200 L/min, such as about 0 to about 100 L/min, such as about 0 to about 75 L/min, such as about 0 to about 50 L/min, such as about 0 to about 25 L/min, such as about 0 to about 20 L/min, such as about 0 to about 15 L/min, such as about 0 to about 10 L/min, such as about 0 to about 5 L/min, and such as about 0 to about 1 L/min. The minimum fluid flow rate through the testing chamber may be zero, obtained either due to successful plugging of the flow restriction(s) or when one or more of the first and second flow control valves are closed. One or more embodiments may achieve a maximum fluid flow rate of up to approximately 4,000 L/min, which reflects the maximum flow rate likely encountered in field scenarios. However, one of ordinary skill in the art may envision configurations of the testing apparatus that may support greater volumetric fluid flow rates.

Some embodiments may include one or more second flow control valves downstream from the first fluid outlet conduit(s), the second fluid outlet conduit(s), or both. Each second control valve may be used as an individual variable choke. One or more second control valve(s) may be used to control the flow rate(s) through the first fluid outlet conduit(s), the second fluid outlet conduit(s), or both. Downstream from the first fluid outlet conduit(s) may be one or more second flow control valves. Similarly, downstream from the second fluid outlet conduit(s) may be one or more second flow control valves. In some embodiments, each fluid outlet conduit may be coupled downstream to a separate second flow control valve. In some embodiments, all fluid control outlets coupled to a single volume (for instance, the annulus or the first chamber interior) may be coupled downstream to a single second flow control valve. In some embodiments, all fluid control outlets of the testing chamber may be coupled downstream to a single second flow control valve. In some embodiments, all fluid control outlets coupled to one volume may be coupled downstream to second flow control valve while all fluid control outlets coupled to another volume may not be flow controlled (meaning may not pass through a second flow control valve). For example, in testing apparatus 800 (FIG. 8), second fluid outlet conduit 19B may be coupled to a second flow control valve 17 (FIG. 12) but first fluid outlet conduit 19A may be coupled to second flow direction valve 15 (FIG. 12).

In some embodiments, each second flow control valve may be independently controlled. By controlling the second flow control valves downstream from one or more of the first and the second fluid outlet conduits, it may be possible to change the fluid flow path within the testing chamber, the flow rate of the fluid passing from the testing chamber, or both. For example, by closing the second flow control valve downstream from the second fluid outlet conduit(s) and opening the second flow control valve downstream from the first fluid outlet conduit(s), only fluid in the annulus may pass from the testing chamber. Alternatively, specific fluid flow rates through the first and the second fluid outlet conduits may be set using second flow control valves. One having skill in the art will appreciate how controlling the flow rates through the first fluid outlet conduit(s), the second fluid outlet conduit(s), or both, may be useful to simulate different downhole flow conditions experienced in a lost circulation zone.

FIG. 13 depicts an LCM testing system according to one or more embodiments.

Testing system 1300 has several aspects that are similar to and described previously in relation to testing system 1200 as shown in FIG. 12. FIG. 13 depicts testing system 1300, which includes a testing apparatus 101 that is one component within two fluidly coupled circuits. The configuration of testing system 1300 may serve to supply up to three different fluids to testing apparatus 101 through a fluid inlet conduit 9 as well as discharging the fluid from testing apparatus 101 via a fluid outlet conduit 19. The three fluids may be selectively supplied in any combination, including simultaneously or separately. In an alternative, one fluid may be supplied from all the supply locations such that testing system 1300 acts with greater fluid flow capacity than testing system 1200. FIG. 13 also shows a device central axis 6 (dashed centralized line) and a general fluid flow direction 8 (arrow).

As seen in FIG. 13, the configuration of testing system 1300 may include three sources of fluid—a first test fluid reservoir 1A, a second test fluid reservoir 1B, and a fluid feed conduit 3—upstream of fluid inlet conduit 9. First and second test fluid reservoirs 1A and 1B may store fluid in advance of a test, similar to test fluid reservoir 1 of testing system 1200. Fluid may come from an outside source, for example, a hose, via fluid feed conduit 3. Selectively directing at least one of these three fluids into testing apparatus 101 may occur via a first flow direction valve 5.

In one or more embodiments, the testing apparatus may have more than one fluid inlet conduit located near an upstream end of the testing chamber. In one or more embodiments, the testing apparatus may have a first fluid inlet conduit and a second fluid inlet. In one or more such embodiments, the fluid into each fluid inlet conduit may come from one or more sources, for example, a first test fluid reservoir, a second test fluid reservoir, or a fluid feed conduit. For example, a first fluid inlet conduit may be directly or indirectly coupled to the first test fluid reservoir and the fluid feed conduit, while a second fluid inlet conduit may be directly or indirectly coupled to the second test fluid reservoir. In another example, each of the three fluid sources may have a dedicated fluid inlet conduit. In such instances, one or more of a flow direction valve and a flow meter may be fluidly located between the fluid source(s) and the fluid inlet conduits of such variant embodiment systems. One having skill in the art will appreciate how to configure and operate such components to fulfil the experimental requirements of embodiments of the testing system.

In one or more embodiments, the first flow control valve may be configured to be controlled by an analog or digital signal such that the flow rate from each of the first test fluid reservoir, the second test fluid reservoir, and the fluid feed conduit are controlled. In one or more embodiments, the first flow control valve may be positioned such that the fluids from the first test fluid reservoir, the second test fluid reservoir, and the fluid feed conduit are mixed at the first flow control valve and simultaneously introduced into the fluid inlet conduit.

Similar to testing system 1200 as shown in FIG. 12, downstream of testing chamber 20 in testing system 1300 there may be a fluid outlet conduit 19 followed by a second flow control valve 17 and a second flow direction valve 15. As shown in FIG. 13, a second flow direction valve 15 may selectively permit the fluid to be sent to a fluid exit conduit 13, a first test fluid collector 11A, or a second test fluid collector 11B.

Testing system 1300 is also configured similarly to testing system 1200 in that it has the option to selectively direct fluids back to the fluid reservoirs. As seen in FIG. 13, the first and the second test fluid return conduits 10A and 10B may fluidly couple first test fluid collector 11A to test fluid reservoir 1A and second test fluid collector 11B to second test fluid reservoir 1B, respectively, in order to capture the fluids once they have passed through testing apparatus 101. This recirculated fluid may be saved for a future test or may be recycled during a test to continuously replenish the first test fluid reservoir, the second fluid reservoir, or both as previously described.

One having skill in the art will appreciate that many of the components depicted in FIGS. 12 and 13 may not be required for a functioning testing system 1200 or 1300. Referring to FIG. 12 for reference, one or more embodiments may not include one or more of test fluid reservoir 1; first and second flow direction valve(s) 5, 15; fluid feed conduit 3; first and second flow control valve(s) 7, 17; fluid exit conduit 13; test fluid collector 11; and test fluid return conduit 10.

Some or all the components described previously and depicted in FIGS. 12 and 13 may be incorporated into embodiments of a testing system 1200 or 1300. Other components not explicitly disclosed here may also be included in testing system 1200 or 1300. In view of the previous discussion and of FIGS. 12 and 13, one having skill in the art will appreciate the many combinations of components both upstream of fluid inlet conduit 9 and downstream of fluid outlet conduit 19 that may be incorporated in-line with one or more embodiments of testing chamber 20 to form testing system 1200 or 1300 according to this disclosure.

One or more embodiments of the testing system may also include one or more appropriately placed sensors, such as pressure, temperature, or flow sensors. In some embodiments, these sensors may be located within the testing apparatus, for example within the testing chamber or the chamber body. Sensors may help detect and numerically characterize the impacts of LCM introduction and the flow mitigation process. In one or more embodiments, a sensor may monitor the conditions within an embodiment of testing apparatus in real-time.

In one or more embodiments, a pressure sensor (not depicted) may be integrated into one or more components of the testing apparatus. In one or more embodiments, pressure sensors within the testing chamber may be both upstream and downstream of the flow restriction(s) to measure the pressure differential across the flow restriction(s). In one or more embodiments, pressure sensor(s) may be integrated into the component defining the flow restriction(s) (for example, the orifice body or the first chamber body) to measure the pressure differential across the flow restriction(s). Measuring the pressure differential across the flow restriction(s) may help monitor the plugging process as well as to help determine a flow rate through the flow restriction(s)

In one or more embodiments, a temperature sensor (not depicted) may be integrated into one or more components of the testing apparatus. In one or more embodiments, temperature sensors within the testing chamber may be both upstream and downstream of the flow restriction(s) to monitor for a potential temperature differential. In one or more embodiments, temperature sensor(s) may be integrated into the component defining the flow restriction(s) (for example, the orifice body or the first chamber body) to monitor for potential temperature changes. Such a temperature change or temperature differential may indicate a chemical reaction between the LCM and the fluid or between deployed LCM materials.

In one or more embodiments, a flow sensor (not depicted) may be integrated into one or more components of the testing apparatus. In one or more embodiments, flow sensors within the testing chamber may be both upstream and downstream of the flow restriction(s) to quantify flow rates through the flow restriction(s). In one or more embodiments, flow sensor(s) may be integrated into the component defining the flow restriction(s) (for example, the orifice body or the first chamber body). Flow sensor(s) may be used to determine the flow rate through the flow restriction(s) or through another portion of the testing apparatus.

In one or more embodiments, a flow rate may be measured at any location along the testing apparatus. In one or more embodiments, the fluid flow rate may be measured upstream of the flow restriction. For example, the fluid flow rate may be detected within the fluid inlet conduit, upstream of the flow restriction within the chamber body, or upstream of the flow restriction within the first chamber interior. As well, the fluid flow rate may be detected at the flow restriction. In some embodiments, the fluid flow rate may be measured downstream of the flow restriction. For example, the fluid flow rate may be detected downstream of the flow restriction within the chamber body, downstream of the flow restriction within the annulus, or within the fluid outlet conduit.

In some embodiments, the testing apparatus may not have any associated sensors. Such a testing apparatus may only allow for visual observation and external optical measurement of the impacts of LCM introduction including the clogging process.

Because of the modular configuration of embodiments of the testing apparatus, a sensor, such as any of the sensors previously described, may be integrated into or removed from an embodiment of the testing apparatus between tests. As well, a sensor may similarly be reconfigured (for example, relocated) within an embodiment of the testing apparatus between tests.

A fluid may traverse an embodiment of the testing apparatus by being introduced into a testing chamber via a fluid inlet conduit, flowing through a chamber body, and then passing out via a fluid outlet conduit. Further, one or more flow restriction may restrict the fluid flowing through the chamber body.

In some embodiments, flowing through the chamber body may involve being introduced into a first chamber interior via the fluid inlet conduit, flowing through a flow passage and into an annulus, and passing out of the testing apparatus via the fluid outlet conduit. In some embodiments, the flow restriction(s) may be located at or proximate to the flow passage. These flow restriction(s) may be defined by an orifice body or the first chamber body. The flow restriction(s) may have any of the forms described previously.

In a field operation, a lost fluid zone may be detected or determined before an LCM is deployed. In one or more embodiments, prior to introduction of the LCM, the fluid may have an initial or first fluid flow rate through the flow restriction(s). This first fluid flow rate may be measured at any location along the testing apparatus. One or more embodiments of the method may include establishing a fluid flow (with no LCM present) through an embodiment of the testing apparatus. In one or more embodiments, a steady-state fluid flow through the chamber body may be established and a first fluid flow rate detected or determined before LCM is introduced.

Any number of fluids may be employed. Fluid(s) introduction into the testing chamber via the fluid inlet conduit via the LCM inlet may occur in series, in parallel (meaning simultaneously), or both. Introduction of fluid(s) from a test fluid reservoir may occur in series, in parallel (meaning simultaneously), or both.

Each fluid may be introduced into the testing chamber via one or more fluid inlet conduit.

In a field operation, a lost fluid zone may then be remediated by the introduction of one or more LCM. One having ordinary skill in the art may appreciate the potential permutations of the method for introducing one or more LCM into the testing chamber.

Introduction of LCM(s) via any inlet may or may not occur until after fluid flow through the testing chamber is established.

Any number of LCMs may be employed.

In one or more embodiments of the method, LCM(s) may be introduced into the testing chamber in solid form, in liquid form, or in an LCM/fluid mixture form, that is pre-mixed with a fluid prior to introduction.

In one or more embodiments, the method may include introducing an LCM/fluid mixture into the chamber interior via the fluid inlet conduit. Thus, some embodiments of the method may include mixing LCM with the fluid upstream from the testing chamber, for example, within the test fluid reservoir. In some such embodiments, LCM may have a diameter sufficiently small to allow the LCM/fluid mixture to flow fluidically through the components upstream from the testing chamber. In some such embodiments, the LCM may form a slurry, a colloid, a sol, or a suspension with the fluid.

In one or more embodiments, the method may include introducing LCM into the chamber interior via the LCM inlet. To allow LCM to move through the LCM inlet, an LCM introduced into the testing chamber via the LCM inlet may have a diameter that is less than the diameter of the LCM inlet.

In one or more embodiments, the method may include mixing LCM with a fluid prior to introduction via the LCM inlet.

Multiple LCMs may be pre-mixed prior to introduction via the LCM inlet, for example, as a mixture of multiple LCMs in solid form or a mixture of a liquid LCM and a solid LCM.

Introduction of LCM(s) from a test fluid reservoir or via the LCM inlet may occur in series in any order, in parallel (meaning simultaneously), or both.

In one or more embodiments, the method may include deploying a sequence of more than one LCM in a prescribed order. In such an embodiment, the LCM may have the same or different forms (for example, liquid or solid), the same or different compositions, the same or different sizes, the same or different shapes, or a combination, but each type of LCM is distinguishable from each other by some physical or chemical characteristic. LCM may be introduced into the chamber interior via the LCM inlet, the fluid inlet conduit, or both. Such a technique may simulate a multi-step loss control remediation procedure.

In some embodiments, the LCM introduced via the LCM inlet may have a larger diameter than the LCM pre-mixed with the fluid prior to introduction into the testing chamber.

In one or more embodiments, after introduction of the LCM, the fluid may have a final or second flow rate through the flow restriction(s). This second flow rate may be detected or determined at any location along the testing apparatus, such as at the same position along the testing apparatus as the detection or determination of the first flow rate. If the flow restriction(s) have been obstructed by the LCM, the second fluid flow rate may be less than the first flow rate, such as a flow rate of about zero.

LCM may require time to fully mitigate fluid flow through the flow passage, perforation, or orifice body. Accordingly, in one or more embodiments, detection or determination of the second flow rate may occur upon achieving a steady-state flow rate has been reached, including a steady-state flow rate of about zero.

While only an first and a second fluid flow rate are described, one or more embodiments may intermittently or continuously monitor the fluid flow rate at one or more locations within the embodiment testing apparatus. Such supplementary monitoring of the fluid flow rate may provide additional informational about the performance of LCM.

In one or more embodiments, one LCM may be at least ten times (10×) larger than the other deployed LCM. In one or more embodiments, the larger LCM may range in size from 5 mm to 38 mm. In one or more embodiments, the one or more flow restrictions may be slightly smaller than the largest LCM being tested and, thus, the flow restriction(s) may be at least 10× larger than the smaller LCM. "Slightly smaller" may mean that the flow restriction(s) may be at least 10% smaller than the LCM (for example, 5% smaller, 2% smaller, or 1% smaller, and ranges in-between).

When the fluid is optically transparent and an embodiment of test chamber that includes optically transparent components are used, optical monitoring such as by video/photo recording or optical sensing may occur. When either a non-transparent test chamber, a non-transparent fluid, or both, are used, sensors such as those to detect flow rate, temperature, or pressure changes, may need to be incorporated, as discussed previously.

The method for testing LCM within the testing apparatus may further include the manipulation of an integrity wiper according to one or more embodiments. In some embodiments, the agitation component of the integrity wiper (for example, a head or a pipe connector) may be moved near the flow passage(s) of a first chamber wall. In some embodiments, the movement of the integrity wiper may be performed using the shaft. Thus, a method of testing LCM may further include movement (for example, axial along the device central axis, rotational) of the integrity wiper near the flow passage(s), such as via manipulation of a shaft that extends out of first chamber interior.

As discussed previously, in one or more embodiments, each of the flow passage(s) 41 may be proximate to a lateral orifice 80 within an annulus 43 between the first chamber wall 40 and a second chamber wall 45. Thus, such agitation may be performed after the orifice inlet(s) 81 of the lateral orifice(s) 80 are clogged with LCM to test the robustness of the clog(s).

The method for testing LCM within an embodiment of the testing apparatus may be performed at less than, at, or greater than room temperature (about 20° Celsius).

Some embodiments of the method may include controlling (increasing, decreasing, or both) the temperature of the fluid(s) prior to introduction into the testing apparatus via the fluid inlet conduit. To that end, the method may include controlling temperature control component(s) that controls the temperature of the fluid(s) upstream from the fluid inlet conduit (for example, in the test fluid reservoir(s), in the fluid feed conduit, or both).

Some embodiments of the method may include controlling (increasing, decreasing, or both) the temperature of one or more temperature control components located proximate to the testing apparatus. In some embodiments, the method may include controlling temperature control component(s) located proximate to the chamber body so as to control the temperature of the fluid and LCM within the chamber interior.

Some embodiments of the method may include performing the test at a pressure at or greater than room pressure (about 14.7 psi).

Some embodiments of the method may include controlling (for example, increasing) the pressure of the fluid(s) prior to introduction into the testing apparatus via the fluid inlet conduit. Thus, in some embodiments, the method may include controlling one or more pressure control components that pressurizes the fluid(s) upstream from the fluid inlet conduit (for example, in the test fluid reservoir(s), in the fluid feed conduit, or both).

Some embodiments of the method may include controlling (for example, increasing) the test pressure in the testing apparatus. Thus, in some embodiments, the method may include controlling pressure control component(s) that pressurize the testing apparatus, for example by applying air backpressure.

Some embodiments of the method may include equalizing the test pressure in the testing apparatus to ambient pressure. Thus, some embodiments may include leaving open to the environment at least one air pressure port or one filling port on the test fluid reservoir.

In some embodiments, the method may include directing fluid(s) from one or more fluid sources (for example, the first or second test fluid reservoirs or the fluid feed conduit), and thus the specific fluid(s), into the fluid inlet conduit. To that end, some embodiments of the method may include controlling the first flow direction valve.

Some embodiments of the method may include controlling the flow rate of the fluid(s) into the fluid inlet conduit. To that end, some embodiments of the method may include controlling the first flow control valve.

Some embodiments of the method may include controlling the second flow direction valve.

In some embodiments, the method may include directing fluids discharged out of the fluid outlet conduit into one or more final location (for example the first or second test fluid collection or the fluid exit conduit). To that end, some embodiments of the method may include controlling the second flow direction valve.

Some embodiments of the method may include controlling the flow rate of the fluid(s) out of the fluid outlet conduit. To that end, some embodiments of the method may include controlling the second flow control valve.

Some embodiments of the method may include controlling components related to the test fluid return conduit(s), for example their accompanying pumps (not depicted). Such a method may be used to be return fluid to a test fluid reservoir from an associated test fluid collector.

Some embodiments of the method may include controlling the initiation and termination a test, for example with the first or second flow control valve.

One having skill in the art will appreciate how the previously disclosed method for testing LCM with the testing apparatus may be further complemented by the methods of use for the testing system components upstream and downstream from the testing apparatus Unless defined otherwise, all technical and scientific terms used have the same meaning as commonly understood by one of ordinary skill in the art to which these systems, apparatuses, methods, processes and compositions belong.

It is noted that one or more of the following claims utilize the term "where" or "in which" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising." For the purposes of defining the present technology, the transitional phrase "consisting of" may be introduced in the claims as a closed preamble term limiting the scope of the claims to the recited components or steps and any naturally occurring impurities. For the purposes of defining the present technology, the transitional phrase "consisting essentially of" may be introduced in the claims to limit the scope of one or more claims to the recited elements, components, materials, or method steps as well as any non-recited elements, components, materials, or method steps that do not materially affect the novel characteristics of the claimed subject matter. The transitional phrases "consisting of" and "consisting essentially of" may be interpreted to be subsets of the open-ended transitional phrases, such as "comprising" and "including," such that any use of an open ended phrase to introduce a recitation of a series of elements, components, materials, or steps should be interpreted to also disclose recitation of the series of elements, components, materials, or steps using the closed terms "consisting of" and "consisting essentially of." For example, the recitation of a composition "comprising" components A, B, and C should be interpreted as also disclosing a composition "consisting of" components A, B, and C as well as a composition "consisting essentially of" components A, B, and C. Any quantitative value expressed in the present application may be considered to include open-ended embodiments consistent with the transitional phrases "comprising" or "including" as well as closed or partially closed embodiments consistent with the transitional phrases "consisting of" and "consisting essentially of."

As used in the Specification and appended Claims, the singular forms "a," "an," and "the" include plural references unless the context clearly indicates the contrary. The verb "comprises" and its conjugated forms should be interpreted as referring to elements, components, or steps in a non-exclusive manner. The referenced elements, components or steps may be present, utilized or combined with other elements, components or steps not expressly referenced.

As used here and in the appended claims, the words "comprise," "has," and "include" and all grammatical variations thereof are each intended to have an open, non-limiting meaning that does not exclude additional elements or steps.

When the word "approximately" or "about" are used, this term may mean that there can be a variance in value of up to ±10%, of up to 5%, of up to 2%, of up to 1%, of up to 0.5%, of up to 0.1%, or up to 0.01%.

The term "substantially" as used refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Ranges may be expressed as from about one particular value to about another particular value, inclusive. When such a range is expressed, it is to be understood that another embodiment is from the one particular value to the other particular value, along with all particular values and combinations thereof within the range.

While the scope of what has been disclosed has been described with respect to a limited number of embodiments, those skilled in the art, having benefit of this disclosure, will appreciate that other embodiments not specifically described can be devised that do not depart from the overall scope as disclosed herein. Accordingly, the scope should be limited only by the attached claims.

What is claimed is:

1. A testing apparatus, comprising:
   a testing chamber having an upstream end, a downstream end, a device central axis, and a general flow direction, comprising:
   a chamber body having an upstream cap, a downstream cap, a first chamber wall, and a second chamber wall, where the first chamber wall has a first diameter and in part defines a first chamber interior, the second chamber wall has a second diameter, the first diameter is less than the second diameter, and both the first chamber wall and the second chamber wall are positioned relative to one another such that an annulus is defined in part in between,
where the upstream cap is proximate to and couples with at least the first chamber wall towards the upstream end,
where the downstream cap is proximate to and couples with at least the first chamber wall towards the downstream end,
where the first chamber wall defines a flow passage such that both a fluid and a lost circulation materials (LCM) may pass from the first chamber interior into the annulus,
where the chamber body further defines a chamber interior, which includes the annulus and the first chamber interior, through which the fluid and the LCM may traverse along a fluid flow path that is at least in part aligned with the general flow direction and the device central axis, and
where traversal of the fluid and the LCM along the fluid flow path is restricted by a flow restriction;
a fluid inlet conduit that is in fluid communication with the first chamber interior and is configured to introduce the fluid into the first chamber interior upstream of the flow passage;
an LCM inlet that is in fluid communication with the first chamber interior and is configured to introduce the LCM into the first chamber interior upstream of the flow passage; and
a fluid outlet conduit that is in fluid communication with the annulus and is configured for passing both the fluid and the LCM from the annulus downstream of the flow passage.

2. The testing apparatus of claim 1, where the flow passage is configured to serve as the flow restriction.

3. The testing apparatus of claim 1, where the fluid flow path through the flow passage is not aligned with either the device central axis or the general flow direction.

4. The testing apparatus of claim 1, where the testing chamber further comprises an orifice body, where the orifice body is configured to serve as the flow restriction, is positioned within the chamber body, and is coupled to the first chamber wall such that the fluid and the LCM must pass through the flow restriction.

5. The testing apparatus of claim 4, where the orifice body is configured to simulate a natural geologic formation.

6. The testing apparatus of claim 4, wherein the orifice body comprises an orifice inlet and an orifice outlet that are not collinear.

7. The testing apparatus of claim 4, where the orifice body comprises a plurality of orifice outlets.

8. The testing apparatus of claim 4, where the orifice body comprises a lateral orifice.

9. The testing apparatus of claim 8, where the lateral orifice is positioned within the annulus such that an orifice inlet is aligned with the flow passage.

10. The testing apparatus of claim 8, where the fluid flow path through the lateral orifice is not aligned with either the device central axis or the general flow direction.

11. The testing apparatus of claim 8, where the lateral orifice is configured with an outlet window opposite an orifice inlet.

12. The testing apparatus of claim 1, further comprising:
an integrity wiper comprising an agitation component coupled to a shaft, where the agitation component of the integrity wiper is positioned within the first chamber interior, where the downstream cap frictionally couples to the shaft to create both a fluid seal and to permit movement of the integrity wiper both axially along the device central axis and rotationally, and where the shaft has a length such that the agitation component of the integrity wiper may axially relocate between upstream and downstream of the flow passage.

13. A method of testing a lost control material (LCM) in a testing apparatus, comprising:
introducing a fluid into the testing apparatus via a fluid inlet conduit such that the fluid has a first fluid flow rate as the fluid traverses a testing chamber of the testing apparatus along a fluid flow path,
where the testing chamber comprises a flow restriction that restricts a traversal of the fluid and the LCM along the fluid flow path,
where the testing chamber comprises a chamber body;
introducing the LCM into the testing apparatus via an LCM inlet such that the LCM traverses the fluid flow path along with the fluid previously introduced and flowing; and
determining a second fluid flow rate of the fluid traversing the fluid flow path after introduction of the LCM.

14. The method of testing LCM according to claim 13, the method further comprising:
inducing a motion in the fluid proximate to a flow passage using an integrity wiper,
where the chamber body further comprises a first chamber wall,
where the first chamber wall defines both a first chamber interior and the flow passage,
where the integrity wiper comprises an agitation component coupled to a shaft,
where the agitation component of the integrity wiper is positioned within the first chamber interior, and
where the shaft has a length such that the agitation component of the integrity wiper may axially relocate between upstream and downstream of the flow passage.

15. A testing system, comprising:
a testing apparatus comprising:
a testing chamber having an upstream end, a downstream end, a device central axis, and a general flow direction, comprising:
a chamber body having an upstream cap, a downstream cap, a first chamber wall, and a second chamber wall,
where the first chamber wall has a first diameter and in part defines a first chamber interior, the second chamber wall has a second diameter, the first diameter is less than the second diameter, and both the first chamber wall and the second chamber wall are positioned relative to one another such that an annulus is defined in part in between,
where the upstream cap is proximate to and couples with at least the first chamber wall towards the upstream end,
where the downstream cap is proximate to and couples with at least the first chamber wall towards the downstream end,
where the first chamber wall defines a flow passage such that both a fluid and a lost circulation materials (LCM) may pass from the first chamber interior into the annulus,
where the chamber body further defines a chamber interior, which includes the annulus and the first chamber interior, through which the fluid and the LCM may traverse along a fluid flow path that is at least in part aligned with the general flow direction and the device central axis, and where traversal of the fluid and the LCM along the fluid flow path is restricted by a flow restriction;

a fluid inlet conduit that is in fluid communication with the first chamber interior and is configured to introduce the fluid into the first chamber interior upstream of the flow passage;

an LCM inlet that is in fluid communication with the first chamber interior and is configured to introduce the LCM into the first chamber interior upstream of the flow passage; and a fluid outlet conduit that is in fluid communication with the annulus and is configured for passing both the fluid and the LCM from the annulus downstream of the flow passage;

a test fluid reservoir fluidly coupled upstream of the testing chamber via the fluid inlet conduit;

a test fluid collector fluidly coupled downstream of the testing chamber via the fluid outlet conduit; and a test fluid return conduit fluidly coupling the test fluid collector to the test fluid reservoir.

16. The testing system of claim 15, where a fluid feed conduit fluidly couples to the testing apparatus via the fluid inlet conduit and a fluid exit conduit fluidly couples to the testing apparatus via the fluid outlet conduit.

17. The testing system of claim 15, where the test fluid reservoir further comprises a first test fluid reservoir and a second test fluid reservoir, where the test fluid collector further comprises a first test fluid collector and a second test fluid collector, and where the test fluid return conduit further comprises a first test fluid return conduit and a second test fluid return conduit, where the first test fluid return conduit fluidly couples the first test fluid reservoir to the first test fluid collector, and where the second test fluid return conduit fluidly couples the second test fluid reservoir to the second test fluid collector.

18. The testing system of claim 15, where the testing system is configured for an operating volumetric fluid flow rate in a range of from about 0 to about 4,000 liters per minute (L/min).

19. The testing system of claim 15, where the testing system is configured for an operating pressure in a range of from about 0 to about 2,500 pounds per square inch (psi).

* * * * *